(12) United States Patent
Milne et al.

(10) Patent No.: US 8,946,451 B2
(45) Date of Patent: Feb. 3, 2015

(54) LIPOIC ACID ACYLATED SALICYLATE DERIVATIVES AND THEIR USES

(75) Inventors: Jill C. Milne, Brookline, MA (US); Michael R. Jirousek, Cambridge, MA (US); Jean E. Bemis, Arlington, MA (US); Chi B. Vu, Arlington, MA (US)

(73) Assignee: Catabasis Pharmaceuticals, Inc., Cambridge, MA (US)

( * ) Notice: Subject to any disclaimer, the term of this patent is extended or adjusted under 35 U.S.C. 154(b) by 237 days.

(21) Appl. No.: 12/898,467

(22) Filed: Oct. 5, 2010

(65) Prior Publication Data
US 2011/0082192 A1    Apr. 7, 2011

Related U.S. Application Data

(60) Provisional application No. 61/248,582, filed on Oct. 5, 2009, provisional application No. 61/308,663, filed on Feb. 26, 2010.

(51) Int. Cl.
| | | |
|---|---|---|
| *C07D 339/02* | (2006.01) | |
| *C07D 341/00* | (2006.01) | |
| *C07D 409/00* | (2006.01) | |
| *A61K 31/60* | (2006.01) | |
| *A61K 31/38* | (2006.01) | |
| *C07D 409/12* | (2006.01) | |
| *A61K 31/385* | (2006.01) | |
| *C07D 339/04* | (2006.01) | |

(52) U.S. Cl.
CPC .......... *C07D 409/12* (2013.01); *A61K 31/385* (2013.01); *C07D 339/04* (2013.01)
USPC ............... 549/35; 549/37; 514/159; 514/161; 514/440; 514/448

(58) Field of Classification Search
USPC .......... 514/440, 159, 161, 448; 549/30, 35, 37
See application file for complete search history.

(56) References Cited

U.S. PATENT DOCUMENTS

| 4,199,576 A | 4/1980 | Reller et al. |
|---|---|---|
| 4,276,430 A | 6/1981 | Reller et al. |
| 6,245,811 B1 | 6/2001 | Horrobin et al. |
| 6,387,945 B2 | 5/2002 | Packer et al. |
| 6,956,077 B1 | 10/2005 | Akiyama et al. |
| RE40,546 E | 10/2008 | Horrobin et al. |
| 7,560,473 B2 | 7/2009 | Wang et al. |
| 2003/0059865 A1* | 3/2003 | Nelson ............................ 435/25 |
| 2007/0155747 A1 | 7/2007 | Dasse et al. |
| 2009/0298923 A1* | 12/2009 | Mian et al. .................... 514/440 |

FOREIGN PATENT DOCUMENTS

| WO | WO9634855 | 11/1996 | |
|---|---|---|---|
| WO | WO/2006/066894 | * 6/2006 | ............. A61K 31/60 |
| WO | WO2009138437 | 11/2009 | |

OTHER PUBLICATIONS

Huang, X. et al., Talanta vol. 78 pp. 1036-1042. Published online Jan. 20, 2009.*
Supplemental Material of Huang, X. et al., Talanta vol. 78 pp. 1036-1042. Published online Jan. 20, 2009.*
Small, D.H., Advances in Behavorial Biology vol. 57 pp. 429-437. Published 2008.*
FDA Guidelines for Pharmaceutically Acceptable Solvents. US Department of Health and Human Services Food and Drug Administration. Published Nov. 2003.*
Zhu, D-H et al., Huaxue Shiji vol. 29, pp. 389-393. Published 2007.*
Huang, X. et al., Talanta vol. 78, pp. 1036-1042. Published online Jan. 20, 2009.*
Zhu, D-H et al., Huaxue Shiji vol. 29, pp. 389-393, published 2007. English Translation Provided.*
Huang, X et al., Talanta vol. 78, pp. 1036-1042, published online Jan. 20, 2009.*
International Search Report and Written Opinion for International Application No. PCT/US10/051491, mailed Nov. 23, 2010, 6 pages.

* cited by examiner

*Primary Examiner* — Paul Zarek
*Assistant Examiner* — George W Kosturko
(74) *Attorney, Agent, or Firm* — Goodwin Procter LLP

(57) ABSTRACT

The invention relates to lipoic acid acylated salicylate derivatives; compositions comprising an effective amount of a lipoic acid acylated salicylate derivative; and methods for treating or preventing an metabolic disease comprising the administration of an effective amount of a lipoic acid acylated salicylate derivative.

20 Claims, No Drawings

LIPOIC ACID ACYLATED SALICYLATE DERIVATIVES AND THEIR USES

This application claims the benefit of U.S. Provisional Application No. 61/248,582, filed Oct. 5, 2009 and U.S. Provisional Application 61/308,663, filed Feb. 26, 2010. The entire disclosures of those applications are relied on and incorporated into this application by reference.

FIELD OF THE INVENTION

The invention relates to lipoic acid acylated salicylate derivatives; compositions comprising an effective amount of a lipoic acid acylated salicylate derivative; and methods for treating or preventing an inflammatory disease comprising the administration of an effective amount of a lipoic acid acylated salicylate derivative. All patents, patent applications, and publications cited herein are hereby incorporated by reference in their entireties.

BACKGROUND OF THE INVENTION

Inflammatory pathways underlie the key pathophysiology of many chronic and acute diseases. Unresolved inflammation is important in many chronic disorders, including, but not limited to, heart disease, atherosclerosis, type 1 and type 2 diabetes, the microvascular complications of diabetes including neuropathy, nephropathy and retinopathy, asthma, arthritis (including rheumatoid arthritis (RA)), osteoarthritis, cystic fibrosis, muscle wasting disease (including muscular dystrophy), pain, insulin resistance, oxidative stress, inflammatory bowel disease (IBD) (including colitis and Crohn's disease), and neurodegenerative disease (including Alzheimer's disease).

In more recent years, the study of inflammation has gone deeper into the cell. Cell-signaling molecules have been identified that modulate the expression of genes that control the inflammatory response, including the pro-inflammatory response and the anti-inflammatory response. One of the central regulators that balance the genes encoding anti- and pro-inflammation factors is Nuclear Factor Kappa Beta (NFκB). NFκB is a family of transcriptions factors that include p50 (NFκB1), p52 (NFκB2), p65 (RelA), c-Rel and RelB. These nuclear factors are held as complexes or dimeric pairs in an inactive state in the cytoplasm as a complex by a NFκB inhibitory factor IκB. The IκB proteins include IκBα, IκBβ, and IκBε, but others also exist. The inactive NFκB complex is released from the cytoplasm by phosphorylation of the IκB protein through kinases such as IKKβ. The kinases regulating NFκB activity are activated by immune responses or cellular stresses. Thus, in the cytoplasmic NFκB complex such as IkB/p65/p50, IkB becomes phosphorylated through kinases such as IKKβ and releases dimeric pairs of NFκB to the nucleus such as p65/p50. In the nucleus, NFκB regulates genetic expression of proinflammatory factors such as cytokines like TNFα, IL-6, and IL-1β in addition to enzymes such as cyclooxygenase-2 (COX-2) one of the enzymes that converts arachidonic acid to prostaglandin H2 (PGH2). These factors induce inflammation in various tissues. In addition, depending upon the cellular context and the NFκB nuclear factors released NFκB can cause the expression of anti-inflammatory genes.

Salicylates and other non-steroidal anti-inflammatory drugs (NSAIDs) can influence the NFκB pathway, allowing people to derive relief and reduced inflammation from these drugs. Aspirin and COX inhibitors act to reduce inflammation by reversibly or irreversibly blocking access to the hydrophobic channel via acetylation of Serine 530 (COX-1) or Serine 516 (COX-2). For some selective NSAIDs with a carboxylate group, there is significant charge-charge interaction with Arginine 120. This binding or interaction blocks the cyclooxygenase enzyme that forms PGH2. Salicylate does not irreversibly inhibit cyclooxygenase because it lacks the ability to acetylate the COX enzyme and has little, if any, direct inhibitory action on the COX enzyme at concentrations that are relevant in vivo. Salicylate has been shown to inhibit the activity of IKKβ and thereby inhibit NFκB leading to reduced expression of COX-2 in an inflammatory state where COX-2 expression has been induced.

Problems arise in salicylate therapy due to side effects, which means alternative ways need to be developed and pursued to reduce NFκB activity. Some salicylates, when given orally, have a key disadvantage of causing gastric ulcers over the long term in chronic administration. In addition, salicylates can be strong irritants, thought to be caused by the high local concentration of these COX inhibitors. Many of the unwanted effects of aspirin are caused by the inappropriate inhibition of COX or the NFκB pathway. Although NSAIDs inhibit COX and are efficacious anti-inflammatory agents, adverse effects limit their use.

Lipoic acid is a dithiol compound found naturally in the body. It plays many important roles such as free radical scavenger, chelator to heavy metals and signal transduction mediator in various inflammatory and metabolic pathways, including the NFκB pathway (Shay, K. P. et al. *Biochim. Biophys. Acta* 2009, 1790, 1149-1160). Lipoic acid has been used to treat diabetic neuropathy and has been shown to also have a positive effect in other diseases that have an underlying etiology of inflammation such as multiple sclerosis, rheumatoid arthritis, ischemic reperfusion, Alzheimer's disease and diabetic neuropathy (Ziegler, D. *Diabetes Metab Res. Rev.* 2008, 24, S52-S57; Salinthone, S. et al. *Endocr., Metab. Immune Disord.: Drug Targets* 2008, 8, 132-142).

The ability to provide the effects of salicylates and lipoic acid in a synergistic way would provide a great benefit in treating the aforementioned diseases.

SUMMARY OF THE INVENTION

The invention is based in part on the discovery of lipoic acid acylated salicylate derivatives and their demonstrated effects in achieving improved treatment that cannot be achieved by administering a salicylate or lipoic acid alone or in combination. These novel compounds are useful in the treatment or prevention of metabolic diseases including atherosclerosis, dyslipidemia, coronary heart disease, hypercholesterolemia, Type 2 diabetes, elevated cholesterol, metabolic syndrome and cardiovascular disease.

Accordingly, in one aspect, a molecular conjugate is described which comprises a salicylate and a lipoic acid covalently linked, wherein the conjugate is capable of hydrolysis to produce free salicylate and free lipoic acid.

Accordingly, in one aspect, compounds of the Formula I are described:

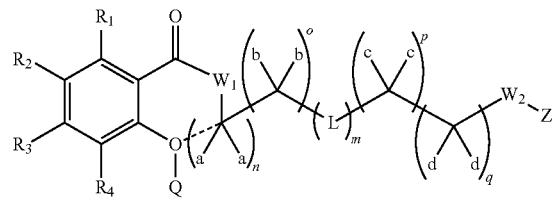

Formula I and pharmaceutically acceptable salts, hydrates, solvates, prodrugs, enantiomers and stereoisomers thereof;

wherein $R_1$, $R_2$, $R_3$, and $R_4$ are each independently selected from the group consisting of H, Cl, F, CN, $NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —C(O)H, —$C(O)C_1$-$C_3$ alkyl, —$C(O)OC_1$-$C_3$ alkyl, —$C(O)NH_2$, —$C(O)NH(C_1$-$C_3$ alkyl), —$C(O)N(C_1$-$C_3$ alkyl)$_2$, —$C_1$-$C_3$ alkyl, —O—$C_1$-$C_3$ alkyl, —$S(O)C_1$-$C_3$ alkyl, and —$S(O)_2C_1$-$C_3$ alkyl;

$W_1$ and $W_2$ are each independently null, O, S, NR, or $W_1$ and $W_2$ can be taken together can form an imidazolidine or piperazine group;

each symbol ----- represents an optional bond, which when present between the phenolic oxygen and the methylene containing substituent a, requires that Q is null, or when present between substituent a and the carbon of the methylene containing substituent a, requires that Q not be null;

each a, b, c, and d is independently —H, -D, —$C_1$-$C_3$ alkyl, —O—$C_1$-$C_3$ alkyl, —C(O)OR, —O—Z, or benzyl, or two of a, b, c, and d can be taken together, along with the single carbon to which they are bound, to form a cycloalkyl or heterocycle;

each n, o, p, and q is independently 0, 1, or 2;

each L is independently —O—, —S—, —S(O)—, —$S(O)_2$—, —S—S—, —($C_1$-$C_6$alkyl)-,

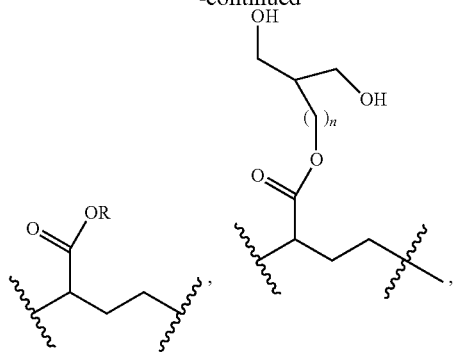

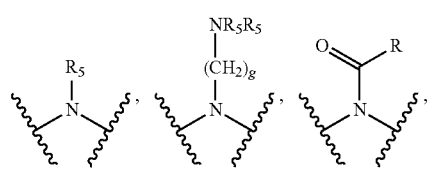

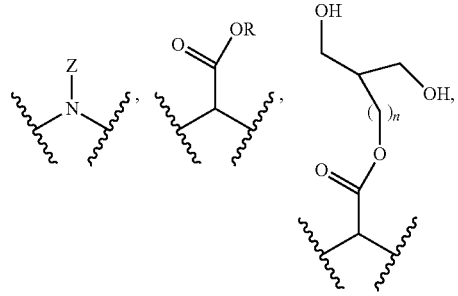

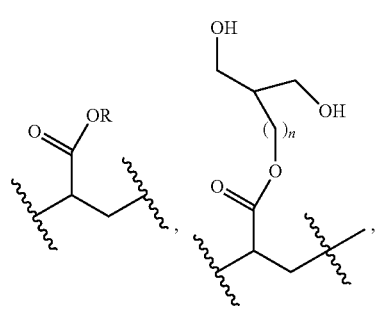

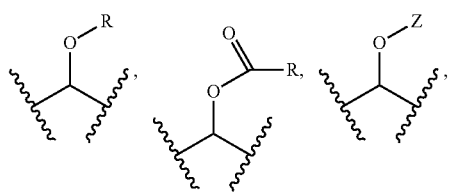

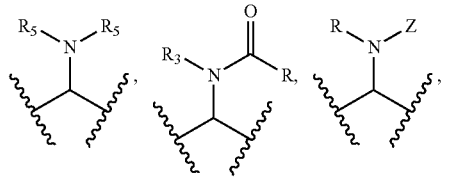

wherein the representation of L is not limited directionally left to right as is depicted, rather either the left side or the right side of L can be bound to the $W_1$ side of the compound of Formula I;

each g is independently 2, 3 or 4;

each h is independently 1, 2, 3 or 4;

m is 0, 1, 2, or 3; if m is more than 1, then L can be the same or different;

each $R_5$ is independently H or $C_1$-$C_6$ alkyl, or both $R_5$ groups, when taken together with the nitrogen to which they are attached, can form a heterocycle;

each $R_6$ is independently e, H, or straight or branched $C_1$-$C_{10}$ alkyl which can be optionally substituted with OH, $NH_2$, $CO_2R$, $CONH_2$, phenyl, $C_6H_4OH$, imidazole or arginine;

each e is independently H or any one of the side chains of the naturally occurring amino acids;

each Z is independently H, or

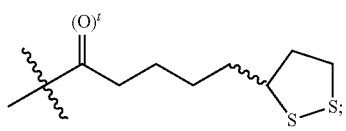

with the proviso that there is at least one

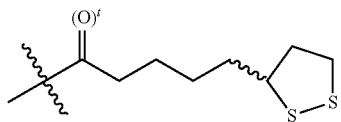

in the compound;
each t is independently 0 or 1;
Q is null, C(O)CH$_3$, Z,

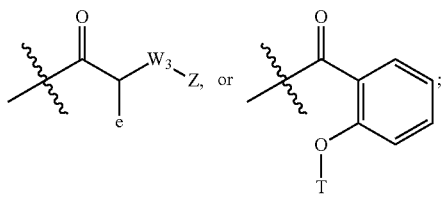

W$_3$ is null, —O—, or —N(R)—;
each R is independently H, —C(O)—C$_1$-C$_3$ alkyl, or straight or branched C$_1$-C$_4$ alkyl optionally substituted with OR, NR$_2$, or halogen; and
T is H, C(O)CH$_3$, or Z;
provided that
when each of m, n, o, p, and q, is 0, W$_1$ and W$_2$ are each null, and Z is

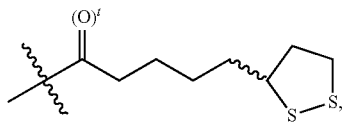

then t must be 0.
Accordingly, in one aspect, compounds of the Formula II are described:

and pharmaceutically acceptable salts, hydrates, solvates, prodrugs, enantiomers and stereoisomers thereof;
wherein
W$_1$, W$_{1'}$, W$_2$ and W$_{2'}$ are each independently null, O, S, NR, or, W$_1$ and W$_2$, or W$_{1'}$ and W$_{2'}$ can be taken together can form an imidazolidine or piperazine group;

each symbol ----- represents an optional bond, which when present between the phenolic oxygen and the methylene containing substituent a, requires that Q is null, or when present between substituent a and the carbon of the methylene containing substituent a, requires that Q not be null;

each a, b, c, and d is independently —H, -D, —C$_1$-C$_3$ alkyl, —O—C$_1$-C$_3$ alkyl, —C(O)OR, —O—Z, or benzyl, or two of a, b, c, and d can be taken together, along with the single carbon to which they are bound, to form a cycloalkyl or heterocycle;

each n, n', o, o', p, p', q, and q' is independently 0, 1, or 2;
each L and L' is independently —O—, —S—, —S(O)—, —S(O)$_2$—, —S—S—, —(C$_1$-C$_6$alkyl)-,

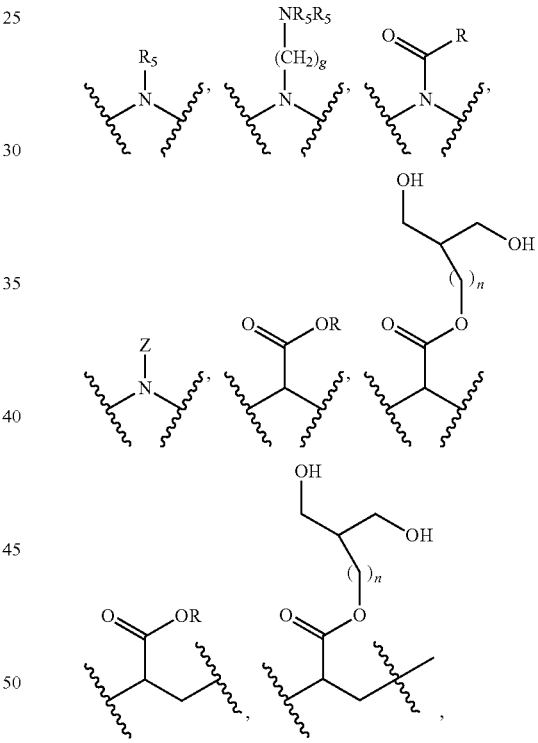

Formula II

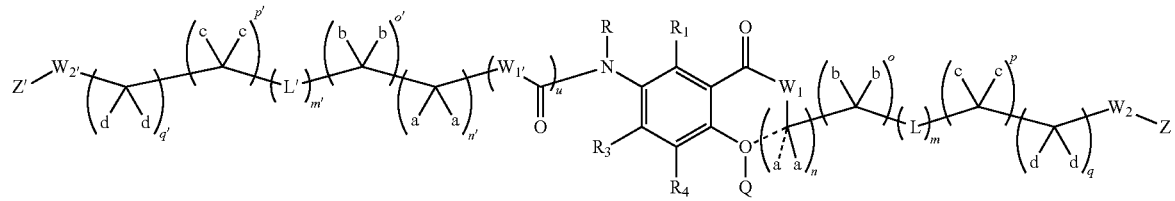

-continued

[chemical structures]

each g is independently 2, 3 or 4;
each h is independently 1, 2, 3 or 4;
each m and m' is independently 0, 1, 2, or 3; if m or m' is more than 1, then L and L' can be the same or different;
each $R_5$ is independently H or $C_1$-$C_6$ alkyl, or both $R_5$ groups, when taken together with the nitrogen to which they are attached, can form a heterocycle;
each $R_6$ is independently e, H, or straight or branched $C_1$-$C_{10}$ alkyl which can be optionally substituted with OH, $NH_2$, $CO_2R$, $CONH_2$, phenyl, $C_6H_4OH$, imidazole or arginine;
each e is independently H or any one of the side chains of the naturally occurring amino acids;
each Z and Z' is independently H, or

[chemical structure]

with the proviso that there is at least one

[chemical structure]

in the compound;
each t is independently 0 or 1;
u is 0 or 1;
Q is null, $C(O)CH_3$, Z,

[chemical structures]

$W_3$ is null, —O—, or —N(R)—;
each R is independently H, —C(O)—$C_1$-$C_3$ alkyl, or straight or branched $C_1$-$C_4$ alkyl optionally substituted with OR, $NR_2$, or halogen; and
T is H, —C(O)$CH_3$, or Z;
provided that
when each of m, n, o, p, and q, is 0, $W_1$ and $W_2$ are each null, and Z is

[chemical structure]

then t must be 0; and
when each of m', n', o', p', and q', is 0, u is 1, $W_{1'}$ and $W_{2'}$ are each null, and Z' is

[chemical structure]

then t must be 0.

Accordingly, in one aspect, compounds of the Formula IIa are described:

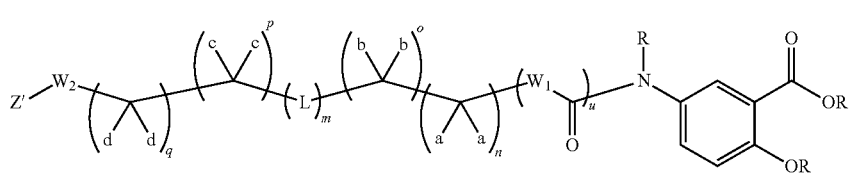

Formula IIa and pharmaceutically acceptable salts, hydrates, solvates, prodrugs, enantiomers and stereoisomers thereof;

wherein $W_1$ and $W_2$ are each independently null, O, S, NR, or $W_1$ and $W_2$ can be taken together can form an imidazolidine or piperazine group;

each a, b, c, and d is independently —H, -D, —$C_1$-$C_3$ alkyl, —O—$C_1$-$C_3$ alkyl, —C(O)OR, —O—Z, or benzyl, or two of a, b, c, and d can be taken together, along with the single carbon to which they are bound, to form a cycloalkyl or heterocycle;

each n, o, p, and q is independently 0, 1, or 2;

each L is independently —O—, —S—, —S(O)—, —S(O)$_2$—, —S—S—, —($C_1$-$C_6$alkyl)-,

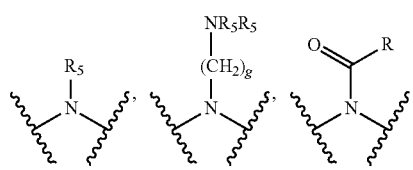

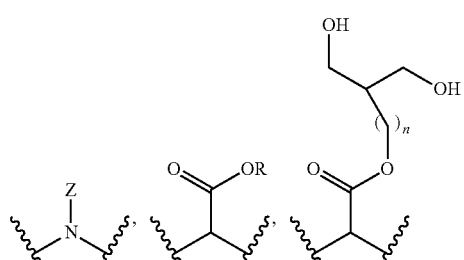

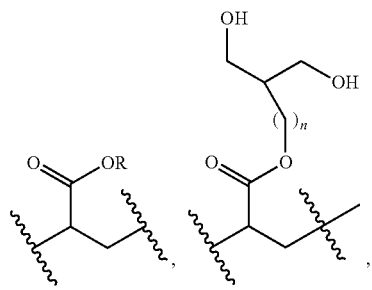

-continued

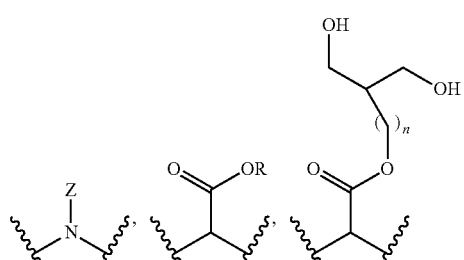

wherein the representation of L is not limited directionally left to right as is depicted, rather either the left side or the right side of L can be bound to the $W_1$ side of the compound of Formula I;

each g is independently 2, 3 or 4;

each h is independently 1, 2, 3 or 4;

m is 0, 1, 2, or 3; if m is more than 1, then L can be the same or different;

each $R_5$ is independently H or $C_1$-$C_6$ alkyl, or both $R_5$ groups, when taken together with the nitrogen to which they are attached, can form a heterocycle;

each $R_6$ is independently e, H, or straight or branched $C_1$-$C_{10}$ alkyl which can be optionally substituted with OH, $NH_2$, $CO_2R$, $CONH_2$, phenyl, $C_6H_4OH$, imidazole or arginine;

each e is independently H or any one of the side chains of the naturally occurring amino acids;

each Z is independently H, or

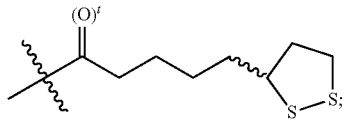

with the proviso that there is at least one

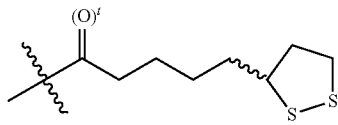

in the compound;
each t is independently 0 or 1;
u is 0 or 1; and
each R is independently H, —C(O)—$C_1$-$C_3$ alkyl, or straight or branched $C_1$-$C_4$ alkyl optionally substituted with OR, $NR_2$, or halogen;
provided that
when each of m, n, o, p, and q, is 0, u is 1, $W_1$ and $W_2$ are each null, and Z is

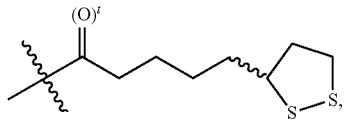

then t must be 0.

In Formula I, Formula II, and Formula IIa, any one or more of H may be substituted with a deuterium. It is also understood in Formula I, Formula II, and Formula IIa, that a methyl substituent can be substituted with a $C_1$-$C_6$ alkyl.

Also described are pharmaceutical formulations comprising at least one lipoic acid acylated salicylate derivative.

Also described herein are methods of treating a disease susceptible to treatment with a lipoic acid acylated salicylate derivative in a patient in need thereof by administering to the patient an effective amount of a lipoic acid acylated salicylate derivative.

Also described herein are methods of treating metabolic diseases by administering to a patient in need thereof an effective amount of a lipoic acid acylated salicylate derivative.

The invention also includes pharmaceutical compositions that comprise an effective amount of a lipoic acid acylated salicylate derivative and a pharmaceutically acceptable carrier. The compositions are useful for treating or preventing a metabolic disease. The invention includes a lipoic acid acylated salicylate derivative provided as a pharmaceutically acceptable prodrug, a hydrate, a salt, such as a pharmaceutically acceptable salt, enantiomer, stereoisomer, or mixtures thereof.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

DETAILED DESCRIPTION OF THE INVENTION

Metabolic diseases are a wide variety of medical disorders that interfere with a subject's metabolism. Metabolism is the process a subject's body uses to transform food into energy. Metabolism in a subject with a metabolic disease is disrupted in some way. The lipoic acid acylated salicylate derivatives possess the ability to treat or prevent metabolic diseases.

The lipoic acid acylated salicylate derivatives have been designed to bring together a salicylate analogs and lipoic acid into a single molecular conjugate. The activity of the lipoic acid acylated salicylate derivatives is substantially greater than the sum of the individual components of the molecular conjugate, suggesting that the activity induced by the lipoic acid acylated salicylate derivatives is synergistic.

DEFINITIONS

The following definitions are used in connection with the lipoic acid acylated salicylate derivatives:

The term "lipoic acid acylated salicylate derivatives" includes any and all possible isomers, stereoisomers, enantiomers, diastereomers, tautomers, pharmaceutically acceptable salts, hydrates, solvates, and prodrugs of the lipoic acid acylated salicylate derivatives described herein.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted.

"$C_1$-$C_3$ alkyl" refers to a straight or branched chain saturated hydrocarbon containing 1-3 carbon atoms. Examples of a $C_1$-$C_3$ alkyl group include, but are not limited to, methyl, ethyl, propyl and isopropyl.

"$C_1$-$C_4$ alkyl" refers to a straight or branched chain saturated hydrocarbon containing 1-4 carbon atoms. Examples of a $C_1$-$C_4$ alkyl group include, but are not limited to, methyl, ethyl, propyl, butyl, isopropyl, isobutyl, sec-butyl and tert-butyl.

"$C_1$-$C_5$ alkyl" refers to a straight or branched chain saturated hydrocarbon containing 1-5 carbon atoms. Examples of a $C_1$-$C_5$ alkyl group include, but are not limited to, methyl, ethyl, propyl, butyl, pentyl, isopropyl, isobutyl, sec-butyl and tert-butyl, isopentyl and neopentyl.

"$C_1$-$C_6$ alkyl" refers to a straight or branched chain saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl and neopentyl.

The term "cycloalkyl" refers to a cyclic hydrocarbon containing 3-6 carbon atoms. Examples of a cycloalkyl group include, but are not limited to, cyclopropyl, cyclobutyl, cyclopentyl and cyclohexyl.

It is understood that any of the substitutable hydrogens on an alkyl or cycloalkyl can be substituted with halogen, $C_1$-$C_3$ alkyl, hydroxyl, alkoxy and cyano groups.

The term "heterocycle" as used herein refers to a cyclic hydrocarbon containing 3-6 atoms wherein at least one of the atoms is an O, N, or S. Examples of heterocycles include, but are not limited to, aziridine, oxirane, thiirane, azetidine, oxetane, thietane, pyrrolidine, tetrahydrofuran, tetrahydrothiophene, piperidine, tetrahydropyran, thiane, imidazolidine, oxazolidine, thiazolidine, dioxolane, dithiolane, piperazine, oxazine, dithiane, and dioxane.

The term "any one of the side chains of the naturally occurring amino acids" as used herein means a side chain of any one of the following amino acids: Isoleucine, Alanine, Leucine, Asparagine, Lysine, Aspartate, Methionine, Cysteine, Phenylalanine, Glutamate, Threonine, Glutamine, Tryptophan, Glycine, Valine, Proline, Arginine, Serine, Histidine, and Tyrosine.

The term "lipoic acid" as used herein means the molecule known as lipoic acid and any derivative thereof.

The term "salicylic acid" as used herein means the molecule known as salicylic acid and any derivative thereof.

The term "salicylate" as used herein means the esters or salts of salicylic acid and any derivative thereof.

A "subject" is a mammal, e.g., a human, mouse, rat, guinea pig, dog, cat, horse, cow, pig, or non-human primate, such as a monkey, chimpanzee, baboon or rhesus, and the terms "subject" and "patient" are used interchangeably herein.

The invention also includes pharmaceutical compositions comprising an effective amount of a lipoic acid acylated salicylate derivative and a pharmaceutically acceptable carrier. The invention includes a lipoic acid acylated salicylate derivative provided as a pharmaceutically acceptable prodrug, hydrate, salt, such as a pharmaceutically acceptable salt, enantiomers, stereoisomers, or mixtures thereof.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "metabolic disease" as used herein refers to disorders, diseases and syndromes involving dyslipidemia, and the terms metabolic disorder, metabolic disease, and metabolic syndrome are used interchangeably herein.

An "effective amount" when used in connection with a lipoic acid acylated salicylate derivative is an amount effective for treating or preventing a metabolic disease.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating", with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a lipoic acid acylated salicylate derivative.

The following abbreviations are used herein and have the indicated definitions: Boc and BOC are tert-butoxycarbonyl, $Boc_2O$ is di-tert-butyl dicarbonate, CDI is 1,1'-carbonyldiimidazole, DCC is N,N'-dicyclohexylcarbodiimide, DIEA is N,N-diisopropylethylamine, DMAP is 4-dimethylaminopyridine, DMSO is dimethyl sulfoxide, DOSS is sodium dioctyl sulfosuccinate, EDC and EDCI are 1-ethyl-3-(3-dimethylaminopropyl)carbodiimide hydrochloride, EtOAc is ethyl acetate, h is hour, HATU is 2-(7-aza-1H-benzotriazole-1-yl)-1,1,3,3-tetramethyluronium hexafluorophosphate, HPMC is hydroxypropyl methylcellulose, LPS is lipopolysaccharide, MCP is monocyte chemotactic protein, oxone is potassium peroxymonosulfate, Pd/C is palladium on carbon, RT is room temperature, TFA is trifluoroacetic acid, TGPS is tocopherol propylene glycol succinate, THF is tetrahydrofuran, TNF is tumor necrosis factor, and VCAM is vascular cell adhesion molecule.

Accordingly in one aspect, the present invention provides a molecular conjugate which comprises a lipoic acid and a salicylate covalently linked, wherein the conjugate is capable of hydrolysis to produce free lipoic acid and free salicylate. In some embodiments, the hydrolysis is enzymatic.

In another aspect, the present invention provides lipoic acid acylated salicylate derivatives according to Formula I:

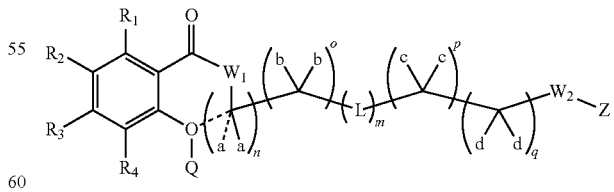

Formula I and pharmaceutically acceptable salts, hydrates, solvates, prodrugs, enantiomers and stereoisomers thereof;
wherein
$R_1$, $R_2$, $R_3$, $R_4$, $R_5$, $R_6$, $W_1$, $W_2$, $W_3$, L, a, b, c, d, e, g, h, m, n, o, p, q, t, Z, R, T and the symbol - - - - - are as defined above for Formula I, and
with the proviso that there is at least one

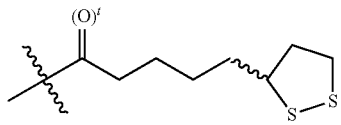

in the compound.

In some embodiments, $R_1$ is H, Cl, F, CN or —CH$_3$, or —CH$_2$CH$_3$.

In some embodiments, $R_2$ is H, Cl, F, CN or —CH$_3$, or —CH$_2$CH$_3$.

In some embodiments, $R_3$ is H, Cl, F, CN or —CH$_3$, or —CH$_2$CH$_3$.

In some embodiments, $R_4$ is H, Cl, F, CN or —CH$_3$, or —CH$_2$CH$_3$.

In some embodiments, $W_1$ is NH.

In some embodiments, $W_2$ is NH.

In some embodiments, $W_1$ is O.

In some embodiments, $W_2$ is O.

In some embodiments, a and c are each independently H, or CH$_3$

In some embodiments, m is 0.

In other embodiments, m is 1.

In some embodiments, L is —S, or —S—S—.

In some embodiments, L is —O—,

In some embodiments, L is

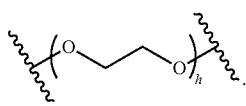

In some embodiments, L is

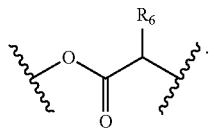

In some embodiments, L is

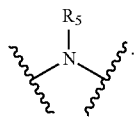

In some embodiments, L is

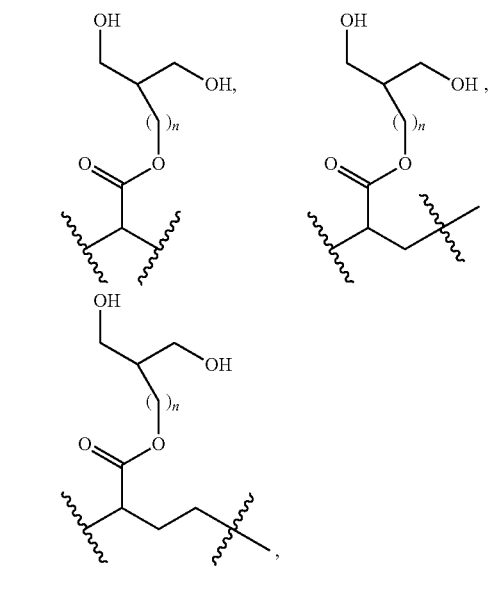

In some embodiments, L is

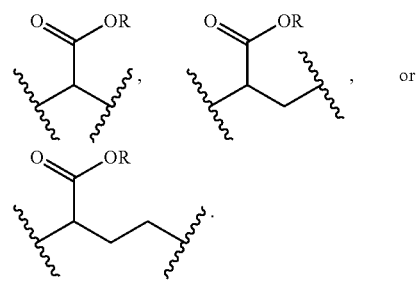

In some embodiments, L is

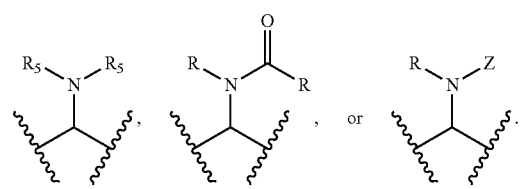

In some embodiments, one d is C(O)OR.

In some embodiments n, o, p, and q are each 1.

In some embodiments, two of n, o, p, and q are each 1.

In other embodiments, three of n, o, p, and q are each 1.

In some embodiments, one Z is

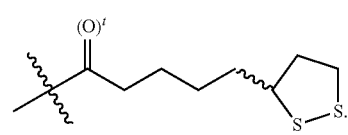

In some embodiments, one Z is

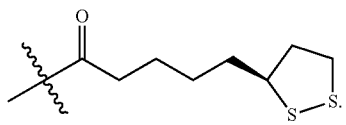 [SMILES: *C(=O)CCCC[C@H]1CCSS1]

In some embodiments, one Z is

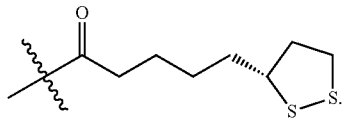 [SMILES: *C(=O)CCCC[C@@H]1CCSS1]

In some embodiments, t is 1.

In some embodiments, $W_1$ is NH, $W_2$ is null, n and o are each 1, p and q are each 0, t is 1, and L is

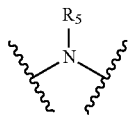

wherein $R_5$ is —H or -D.

In some embodiments, $W_1$ and $W_2$ are each NH, n, o, p and q are each 1, t is 1, and L is —S—S—.

In some embodiments, $W_1$ and $W_2$ are each NH, n, o, p and q are each 1, t is 1, and L is —O—.

In some embodiments, $W_1$ and $W_2$ are each NH, n, o, p and q are each 1, t is 1, and L is

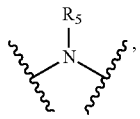

wherein R5 is $C_1$-$C_3$ alkyl.

In some embodiments, $W_1$ and $W_2$ are each NH, n, o, and q are each 1, p is 0, t is 1, one of a is —C(O)OR, one of b is —$C_1$-$C_3$ alkyl, and L is

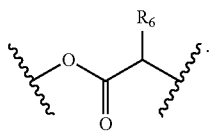

In some embodiments, $W_1$ and $W_2$ are each NH, n, o, and q are each 1, p is 0, t is 1, one of a is —C(O)OR, one of b is —$C_1$-$C_3$ alkyl, and L is

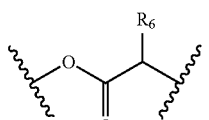

wherein R is —$CH_3$, —$CH_2CH_3$, and b is —$CH_3$.

In some embodiments, $W_1$ and $W_2$ are each NH, n, o, and q are each 1, p is 0, t is 1, one of a is —C(O)OR, one of b is —$C_1$-$C_3$ alkyl, and L is

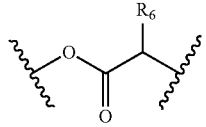

wherein R, $R_6$, and b are each —$CH_3$.

In some embodiments, $W_1$ and $W_2$ are each NH, n, o, p, and q are each 1, t is 1, and L is

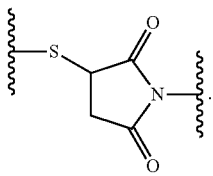 [SMILES: *SC1CC(=O)N(*)C1=O]

In some embodiments, $W_1$ and $W_2$ are each NH, m is 1, n and o are each 0, p and q are each 1, and L is

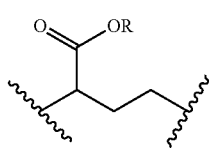

wherein R is —$C_1$-$C_3$ alkyl.

In some embodiments, $W_1$ and $W_2$ are each NH, m is 1, n and o are each 1, p and q are each 0, and L is

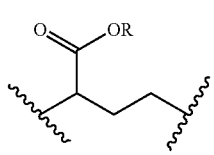

wherein R is —H or -D.

In some embodiments, $W_1$ and $W_2$ are each NH, m is 1, n and o are each 1, p and q are each 0, and L is

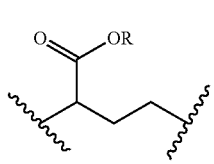

wherein R is —$C_1$-$C_3$ alkyl.

In some embodiments, $W_1$ and $W_2$ are each NH, m is 1, n and o are each 0, p and q are each 1, and L is

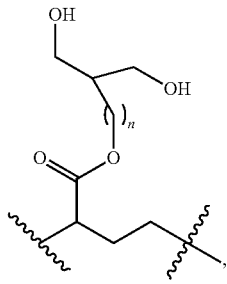

In some embodiments, $W_1$ and $W_2$ are each NH, m is 1, n and o are each 1, p, and q are each 0, and L is

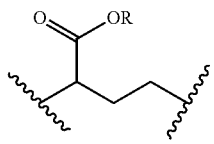

In some embodiments, $W_1$ and $W_2$ are each NH, m is 1, n and o are each 1, p, and q are each 0, and L is

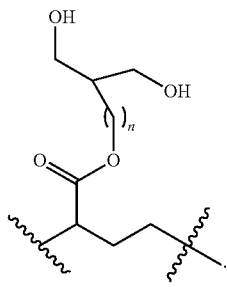

In some embodiments, $W_1$ and $W_2$ are each NH, m is 1, n, o, p, and q are each 0, and L is

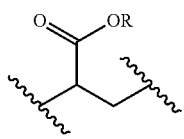

wherein R is —$C_1$-$C_3$ alkyl.

In some embodiments, $W_1$ and $W_2$ are each NH, m is 1, n, o, p, and q are each 0, and L is

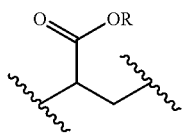

wherein R is —H or -D.

In some embodiments, $W_1$ and $W_2$ are each NH, m is 1, n, o, p, and q each 0, and L is

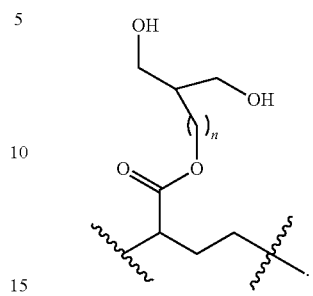

In some embodiments, $W_1$ and $W_2$ are each NH, m is 1, n, o, p, and q are each 1, and L is

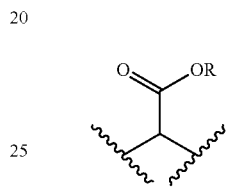

wherein R is —H or -D.

In some embodiments, $W_1$ and $W_2$ are each NH, m is 1, n, o, p, and q are each 1, and L is

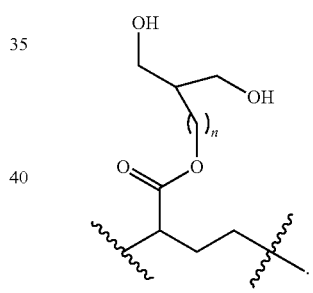

In some embodiments, $W_1$ and $W_2$ are each NH, n, o, and p are each 1, q and m are each 0.

In some embodiments, $W_1$ and $W_2$ are each NH, n and o are each 1, p, q and m are each 0, and each of a is —$CH_3$.

In some embodiments, $W_1$ and $W_2$ are each NH, m is 1, n, o, q, and p are each 1, and m is 0

In some embodiments, $W_1$ and $W_2$ are each NH, n and o are each 1, p, q and m are each 0, and each of b is —$CH_3$ In some embodiments, $W_1$ and $W_2$ are each NH, m, n, o, p, and q are each 1, and L is NH.

In some embodiments, $W_1$ and $W_2$ are each NH, m, n, o, p, and q are each 1, and.

In some embodiments, r is 3, s is 5, and n, o, p, and q are each 1.

In some embodiments, r is 3, s is 5, and two of n, o, p, and q are each 1.

In some embodiments, r is 3, s is 5, and $W_1$ and $W_2$ are each NH.

In some embodiments, $W_1$ and $W_2$ are each NH, m, n, o, p, and q are each 1, and L is

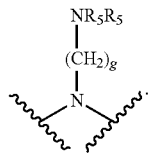

In some embodiments, $W_1$ and $W_2$ are each NH, m, n, o, p, and q are each 1, and L is

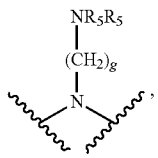

wherein the $R_5$ groups are taken together with the nitrogen to which they are attached to form a heterocycle.

In some embodiments, $W_1$ and $W_2$ are each NH, m, n, o, p, and q are each 1, and L is

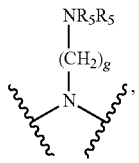

wherein g is 2, and the $R_5$ groups are taken together with the nitrogen to which they are attached to form

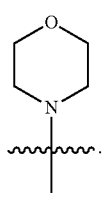

In some embodiments, $W_1$ and $W_2$ are each NH, m, n, o, p, and q are each 1, and L is

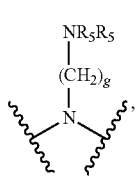

wherein g is 3, and the $R_5$ groups are taken together with the nitrogen to which they are attached to form

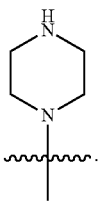

In some embodiments, r is 3, s is 5, m is 1, n, o, p, and q are each 0, and L is

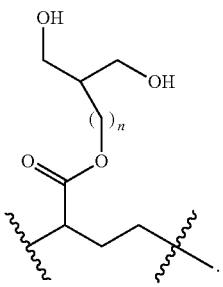

In some embodiments, $W_1$ and $W_2$ are each NH, m, n, and p are each 1, and p and q are each 0, and L is

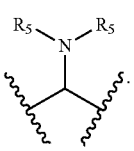

In some embodiments, $W_1$ and $W_2$ are each NH, m, n, and p are each 1, and p and q are each 0, and L is

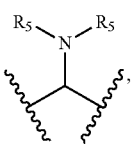

wherein the $R_5$ groups are taken together with the nitrogen to which they are attached to form

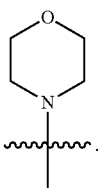

In some embodiments, $W_1$ and $W_2$ are each NH, m, n, and p are each 1, and p and q are each 0, and L is

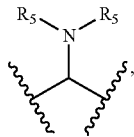

wherein the $R_5$ groups are taken together with the nitrogen to which they are attached to form

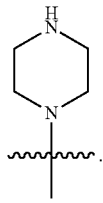

In some embodiments, m, n, o, p, and q are each 1, and L is

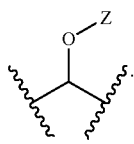

In some embodiments, m, n, o, p, and q are each 1, and L is

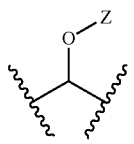

wherein Z is —H or -D.

In some embodiments, $W_1$ and $W_2$ are each NH, m, n, o, p, and q are each 1, and L is

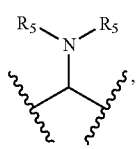

wherein the $R_5$ groups are taken together with the nitrogen to which they are attached to form

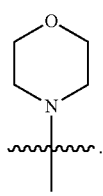

In some embodiments, $W_1$ and $W_2$ are each NH, m, n, o, p, and q are each 1, and L is

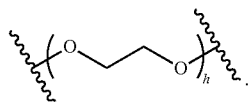

In some embodiments, $W_1$ and $W_2$ are each NH, m, n, o, p, and q are each 1, and L is

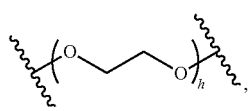

wherein h is 1.

In some embodiments, $W_1$ and $W_2$ are each NH, m, n, o, p, and q are each 1, and L is S.

In other illustrative embodiments, compounds of Formula I are as set forth below:

(S)—N-(2-(5-(1,2-dithiolan-3-yl)pentanamido)ethyl)-2-hydroxybenzamide (I-1), (S)—N-(2-(2-(2-(5-(1,2-dithiolan-3-yl)pentanamido)ethyl) disulfanyl)ethyl)-2-hydroxybenzamide (I-2), (S)—N-(2-(2-(5-(1,2-dithiolan-3-yl)pentanamido)ethoxy) ethyl)-2-hydroxybenzamide (I-3), (S)—N-(2-((2-(5-(1,2-dithiolan-3-yl)pentanamido)ethyl) (methyl)amino)ethyl)-2-hydroxybenzamide (I-4), methyl 3-(2-(5-(1,2-dithiolan-3-yl)pentanamido)acetoxy)-2-(2-hydroxybenzamido)butanoate (I-5), N-(2-(1-(2-(5-(1,2-dithiolan-3-yl)pentanamido)ethyl)-2,5-dioxopyrrolidin-3-ylthio)ethyl)-2-hydroxybenzamide (I-6), methyl 6-(5-(1,2-dithiolan-3-yl)pentanamido)-2-(2-hydroxybenzamido)hexanoate (I-7), 6-(5-(1,2-dithiolan-3-yl)pentanamido-2-(2-hydroxybenzamido)hexanoic acid (I-8), 3-hydroxy-2-(hydroxymethyl)propyl 6-(5-(1,2-dithiolan-3-yl)pentanamido)-2-(2-hydroxybenzamido)hexanoate (I-9), methyl 2-(5-(1,2-dithiolan-3-yl)pentanamido)-6-(2-hydroxybenzamido)hexanoate (I-10), 2-(5-(1,2-dithiolan-3-yl)pentanamido)-6-(2-hydroxybenzamido)hexanoic acid (I-11), 3-hydroxy-2-(hydroxymethyl)propyl 2-(5-(1,2-dithiolan-3-yl)pentanamido)-6-(2-hydroxybenzamido)hexanoate (I-12), methyl 3-(5-(1,2-dithiolan-3-yl)pentanamido)-2-(2-hydroxybenzamido)propanoate (I-13), 3-(5-(1,2-dithiolan-3-yl)pentanamido)-2-(2-hydroxybenzamido)propanoic acid (I-14), 3-hydroxy-2-(hydroxymethyl)propyl 3-(5-(1,2-dithiolan-3-yl)pentanamido)-2-(2-hydroxybenzamido)propanoate (I-15), 2-(5-(1,2-dithiolan-3-yl)pentanamido)-3-(2-hydroxybenzamido)propanoic acid (I-16), 3-hydroxy-2-(hydroxymethyl)propyl 2-(5-(1,2-dithiolan-3-yl)pentanamido)-3-(2-hydroxybenzamido)propanoate (I-17), 2-(2-(5-(1,2-dithiolan-3-yl)pentanamido)ethyl)-4-(2-hydroxybenzamido)butanoic acid (I-18), 3-hydroxy-2-(hydroxymethyl)propyl 2-(2-(5-(1,2-dithiolan-3-yl)pentanamido)ethyl)-4-(2-hydroxybenzamido)butanoate (I-19),
N-(3-(5-(1,2-dithiolan-3-yl)pentanamido)propyl)-2-hydroxybenzamide (I-20),
N-(4-(5-(1,2-dithiolan-3-yl)pentanamido)butyl)-2-hydroxybenzamide (I-21),
N-(1-(5-(1,2-dithiolan-3-yl)pentanamido)-2-methylpropan-2-yl)-2-hydroxybenzamide (I-22),
N-(2-(5-(1,2-dithiolan-3-yl)pentanamido)-2-methylpropyl)-2-hydroxybenzamide (I-23),
N-(2-(2-(5-(1,2-dithiolan-3-yl)pentanamido)ethylamino)ethyl)-2-hydroxybenzamide (I-24),
N-(3-(2-(5-(1,2-dithiolan-3-yl)pentanamido)ethylamino)propyl)-2-hydroxybenzamide (I-25),
N-(2-(3-(5-(1,2-dithiolan-3-yl)pentanamido)propylamino)ethyl)-2-hydroxybenzamide (I-26),
N-(2-((3-(5-(1,2-dithiolan-3-yl)pentanamido)propyl)(ethyl)amino)ethyl)-2-hydroxybenzamide (I-27),
N-(2-(N-(3-(5-(1,2-dithiolan-3-yl)pentanamido)propyl)acetamido)ethyl)-2-hydroxybenzamide (I-28),
N-(2-((2-(5-(1,2-dithiolan-3-yl)pentanamido)ethyl)(2-morpholinoethyl)amino)ethyl)-2-hydroxybenzamide (I-29),
N-(2-((2-(5-(1,2-dithiolan-3-yl)pentanamido)ethyl)(3-(piperazin-1-yl)propyl)amino)ethyl)-2-hydroxybenzamide (I-30),
N-(3-(5-(1,2-dithiolan-3-yl)pentanamido)-2-oxopropyl)-2-hydroxybenzamide (I-31),
N-(3-(5-(1,2-dithiolan-3-yl)pentanamido)-2-morpholinopropyl)-2-hydroxybenzamide (I-32),
N-(3-(5-(1,2-dithiolan-3-yl)pentanamido)-2-(piperazin-1-yl)propyl)-2-hydroxybenzamide (I-33),
N-(5-(5-(1,2-dithiolan-3-yl)pentanamido)-3-hydroxypentyl)-2-hydroxybenzamide (I-34),
N-(5-(5-(1,2-dithiolan-3-yl)pentanamido)-3-morpholinopentyl)-2-hydroxybenzamide (I-35),
N-(2-(2-(2-(5-(1,2-dithiolan-3-yl)pentanamido)ethoxy)ethoxy)ethyl)-2-hydroxybenzamide (I-36), and
N-(2-(2-(5-(1,2-dithiolan-3-yl)pentanamido)ethylthio)ethyl)-2-hydroxybenzamide (I-37).

Described herein are compounds of the Formula II:

and
with the proviso that there is at least one

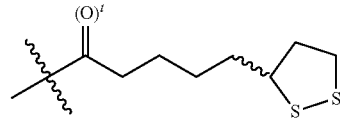

in the compound.

In some embodiments, $W_1$ is NH.
In some embodiments, $W_2$ is NH.
In some embodiments, $W_{1'}$ is NH.
In some embodiments, $W_{2'}$ is NH.
In some embodiments, $W_1$ is O.
In some embodiments, $W_2$ is O.
In some embodiments, $W_{1'}$ is O.
In some embodiments, $W_{2'}$ is.

In some embodiments, one symbol ----- represents a bond. In some embodiments, the bond is present between the phenolic oxygen and the methylene containing substituent a. In other embodiments, the bond is present between substituent a and the carbon of the methylene containing substituent a.

In some embodiments, a and c are each independently H, or $CH_3$.

In some embodiments, m is 0.
In some embodiments, m' is 0.
In some embodiments, m is 1.
In some embodiments, m' is 1.
In some embodiments, each L is independently —S— or —S—S—.
In some embodiments, each L' is independently —S— or —S—S—.
In some embodiments, each L is independently —O—.

Formula II

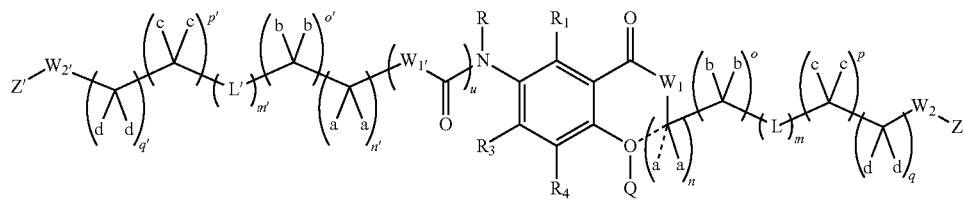

and pharmaceutically acceptable salts, hydrates, solvates, prodrugs, enantiomers, and stereoisomers thereof;

wherein
$R_1$, $R_3$, $R_4$, $R_5$, $R_6$, $W_1$, $W_{1'}$, $W_2$, $W_{2'}$, $W_3$, L, a, b, c, d, e, g, h, m, m', n, n', o, o', p, p', q, q', t, u, Q, T, Z, Z', R, and the symbol ----- are as defined above for Formula II, In some embodiments, each L is independently

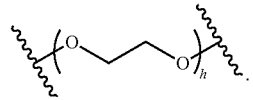

In some embodiments, each L is independently

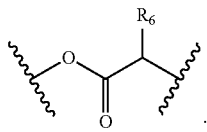

In some embodiments, each L' is independently —O—.
In some embodiments, each L' is independently

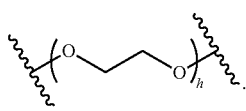

In some embodiments, each L' is independently

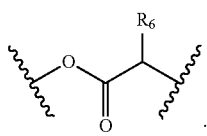

In some embodiments, each L is independently

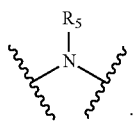

In some embodiments, each L' is independently

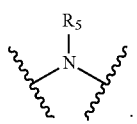

In some embodiments, each L is independently

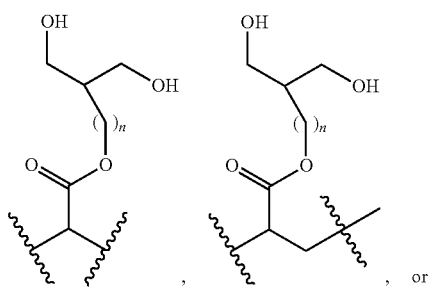

, or

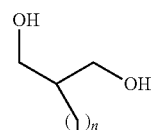

In some embodiments, each L is independently

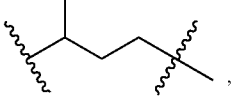

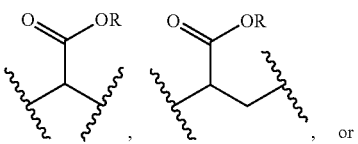

, or

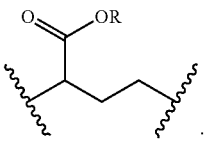

In some embodiments, each L' is independently

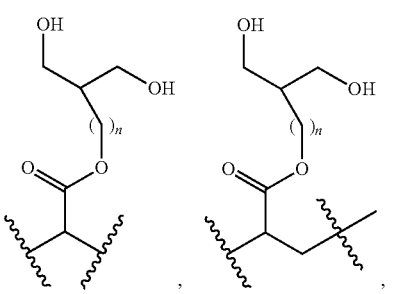

, or

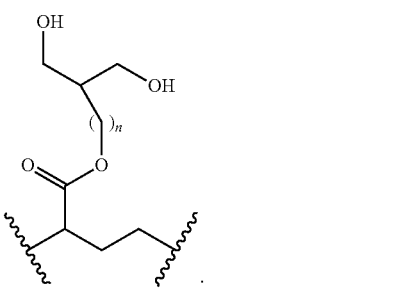

In some embodiments, each L' is independently

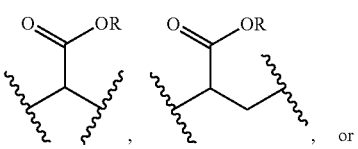

, or

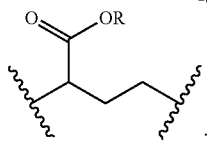

In some embodiments, each L is independently

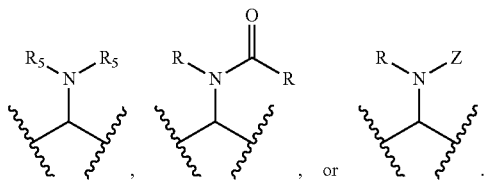

In some embodiments, each L' is independently

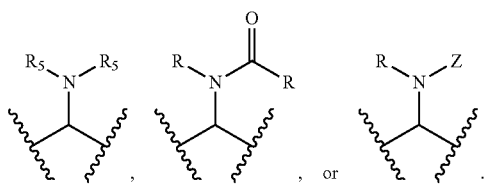

In some embodiments, one b is O—Z and Z is

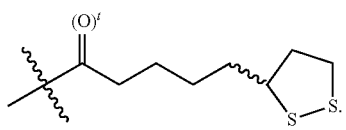

In some embodiments n, o, p, and q are each 1.
In some embodiments n', o', p', and q' are each 1.
In some embodiments, two of n, o, p, and q are each 1.
In other embodiments, three of n, o, p, and q are each 1.
In some embodiments, two of n', o', p', and q' are each 1.
In other embodiments, three of n', o', p', and q' are each 1.
In some embodiments, one of n, o, p, and q is 1.
In other embodiments, one of n', o', p', and q' is 1.
In some embodiments, one Z is

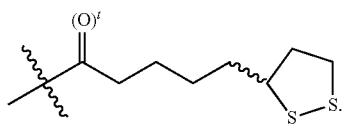

In some embodiments, one Z is

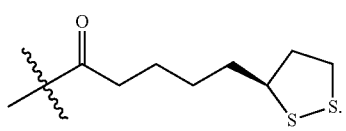 [SMILES: *C(=O)CCCC[C@H]1CCSS1]

In some embodiments, one Z is

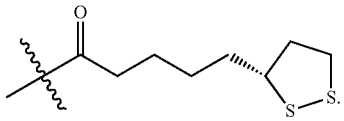 [SMILES: *C(=O)CCCC[C@@H]1CCSS1]

In some embodiments, one Z' is

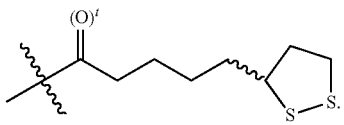

In some embodiments, one Z' is

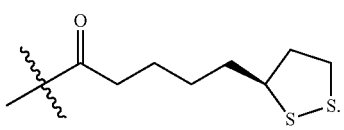 [SMILES: *C(=O)CCCC[C@H]1CCSS1]

In some embodiments, one Z' is

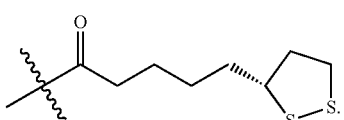

In some embodiments, Q is C(O)CH$_3$
In some embodiments, Q is Z.
In some embodiments, Q is

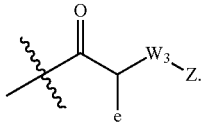

In some embodiments, Q is

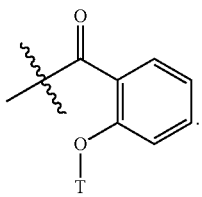

In some embodiments, T is H. In other embodiments, T is C(O)CH$_3$. In other embodiments, T is Z.
In some embodiments, e is any one of the side chains of the naturally occurring amino acids.
In some embodiments, e is H.
In some embodiments, m, n, o, p, and q are each 0, W$_1$ and W$_2$ are each null, Q is —H or -D, m', n', o', p' and q' are each 0, W$_{1'}$ and W$_{2'}$ are each null and u is 0.

In some embodiments, m, n, o, p, and q are each 0, $W_1$ and $W_2$ are each null, Q is —H or -D, m', n', p' and q' are each 1, o' is 0, $W_{1'}$ is null, $W_{2'}$ is NH, u is 1 and L is —S—S—.

In some embodiments, m, n, o, p, and q are each 0, $W_1$ and $W_2$ are each null, Q is —H or -D, m', n', o', p' and q' are each 1, $W_{1'}$ is null, $W_{2'}$ is NH, u is 1 and L is —O—.

In some embodiments, m, n, o, p, and q are each 0, $W_1$ and $W_2$ are each null, Q is —H or -D, m', n', o', p' and q' are each 1, $W_{1'}$ is null, $W_{2'}$ is NH, u is 1 and L is

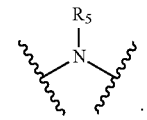

In some embodiments, m, n, o, p, and q are each 0, $W_1$ and $W_2$ are each null, Q is —H or -D, m', n', o', p' and q' are each 1, $W_{1'}$ is null, $W_{2'}$ is NH, u is 1 and L is

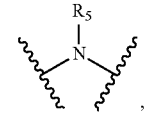

wherein $R_5$ is —H or -D.

In some embodiments, m, n, o, p, and q are each 0, $W_1$ and $W_2$ are each null, Q is —H or -D, m' and q' are each 0, n', o', and p' are each 1, $W_{1'}$ is null, $W_{2'}$ is NH, u is 1 and one of c is —C(O)OR.

In some embodiments, m, n, o, p, and q are each 0, $W_1$ and $W_2$ are each null, Q is —H or -D, m' and q' are each 0, n', o', and p' are each 1, $W_{1'}$ is null, $W_{2'}$ is NH, u is 1 and one of c is —C(O)OR, wherein R is —H or -D.

In some embodiments, m, n, o, p, and q are each 0, $W_1$ and $W_2$ are each null, Q is —H or -D, m', o', and q' are each 0, n' and p' are each 1, $W_{1'}$ is null, $W_{2'}$ is NH, u is 1 and one of c is —C(O)OR.

In some embodiments, m, n, o, p, and q are each 0, $W_1$ and $W_2$ are each null, Q is —H or -D, m', o', and q' are each 0, n' and p' are each 1, $W_{1'}$ is null, $W_{2'}$ is NH, u is 1 and one of c is —C(O)OR, wherein R is —H or -D.

In some embodiments, m, n, o, p, and q are each 0, $W_1$ and $W_2$ are each null, Q is —H or -D, o' is 0, m', n', p' and q' are each 1, $W_{1'}$ is null, $W_{2'}$ is NH, u is 1 and L is

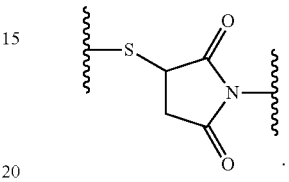

In other illustrative embodiments, compounds of Formula II are as set forth below:

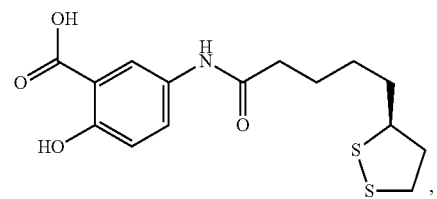 [SMILES: O=C(CCCC[C@H]1CCSS1)Nc1ccc(O)c(C(=O)O)c1]

(S)-5-(5-(1,2-dithiolan-3-yl)pentanamido)-2-hydroxybenzoic acid (II-1)

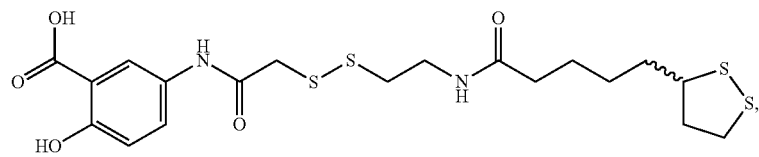 [SMILES: O=C(CCCCC1CCSS1)NCCSSCC(=O)Nc1ccc(O)c(C(=O)O)c1]

5-(2-(2-(2-(5-(1,2-dithiolan-3-yl)pentanamido)ethyl)disulfanyl)acetamido)-2-hydroxybenzoic acid (II-2)

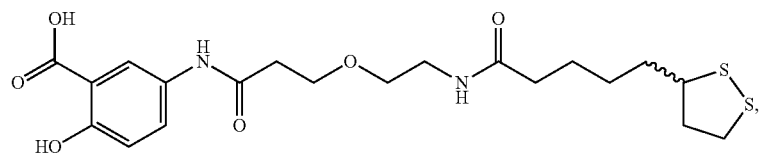 [SMILES: O=C(CCCCC1CCSS1)NCCOCCC(=O)Nc1ccc(O)c(C(=O)O)c1]

5-(3-(2-(5-(1,2-dithiolan-3-yl)pentanamido)ethoxy)propanamido)-2-hydroxybenzoic acid (II-3)

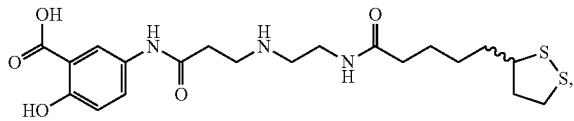 [SMILES: O=C(CCCCC1CCSS1)NCCNCCC(=O)Nc1ccc(O)c(C(=O)O)c1]

5-(3-(2-(5-(1,2-dithiolan-3-yl)pentanamido)ethylamino)propanamido)-2-hydroxybenzoic acid (II-4)

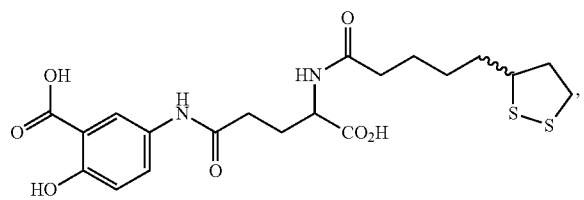 [SMILES: O=C(CCC(NC(=O)CCCCC1CCSS1)C(=O)O)Nc1ccc(O)c(C(=O)O)c1]

5-(4-(5-(1,2-dithiolan-3-yl)pentanamido)-4-carboxybutanamido)-2-hydroxybenzoic acid (II-5)

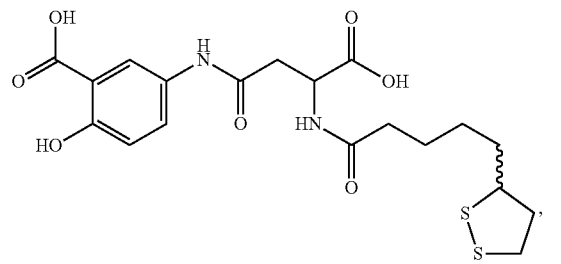 [SMILES: O=C(CC(NC(=O)CCCCC1CCSS1)C(=O)O)Nc1ccc(O)c(C(=O)O)c1]

5-(3-(5-(1,2-dithiolan-3-yl)pentanamido)-3-carboxypropanamido)-2-hydroxybenzoic acid (II-6)

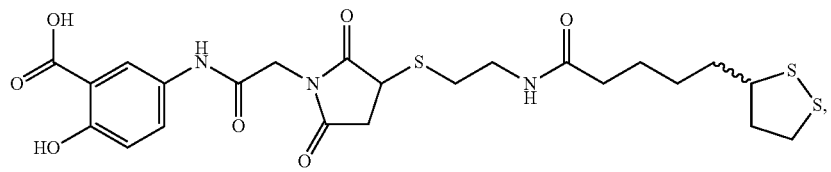 [SMILES: O=C(CCCCC1CCSS1)NCCSC1CC(=O)N(CC(=O)Nc2ccc(O)c(C(=O)O)c2)C1=O]

5-(2-(3-(2-(5-(1,2-dithiolan-3-yl)pentanamido)ethylthio)-2,5-dioxopyrrolidin-1-yl)acetamido)-2-hydroxybenzoic acid (II-7)

Accordingly, in one aspect, compounds of the Formula IIa are described:

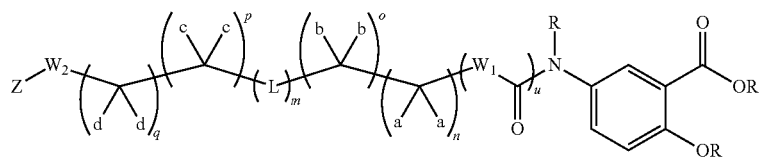

Formula IIa and pharmaceutically acceptable salts, hydrates, solvates, prodrugs, enantiomers and stereoisomers thereof;

wherein $R_1, R_2, R_3, R_4, R_5, R_6, W_1, W_2, L, a, b, c, d, e, g, h, m, n, o, p, q, t, u, Z$, and R are as defined above for Formula IIa, and with the proviso that there is at least one

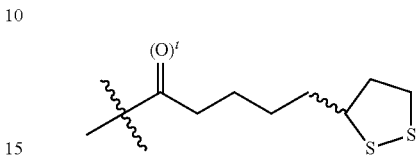

in the compound.

In some embodiments, $W_1$ is NH.
In some embodiments, $W_2$ is NH.
In some embodiments, $W_1$ is O.
In some embodiments, $W_2$ is O.
In some embodiments, a and c are each independently H, or $CH_3$
In some embodiments, m is 0.
In other embodiments, m is 1.
In some embodiments, L is —S, or —S—S—.
In some embodiments, L is —O—,
In some embodiments, L is

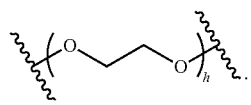

In some embodiments, L is

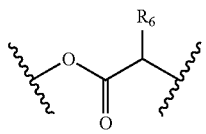

In some embodiments, L is

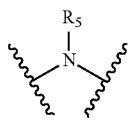

In some embodiments, L is

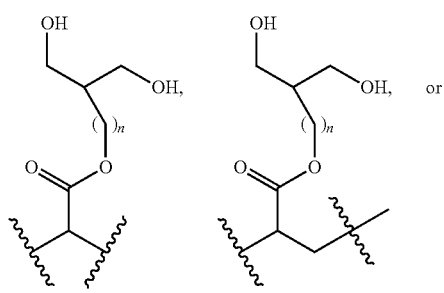

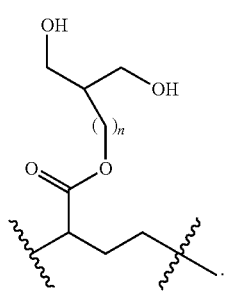

In some embodiments, L is

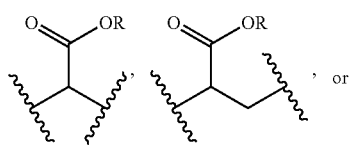

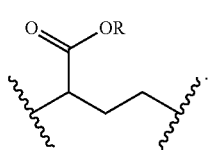

In some embodiments, L is

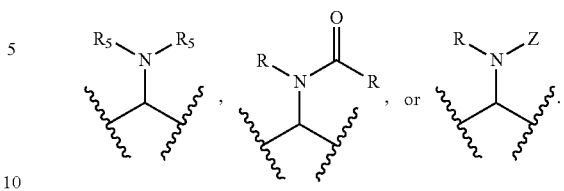

In some embodiments, one b is O—Z, Z is

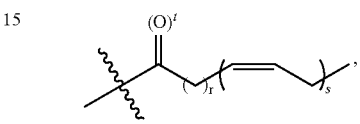

and t is 1.
In some embodiments, one d is C(O)OR.
In some embodiments n, o, p, and q are each 1.
In some embodiments, two of n, o, p, and q are each 1.
In other embodiments, three of n, o, p, and q are each 1.
In some embodiments, one of n, o, p, and q is 1.
In some embodiments, one Z is

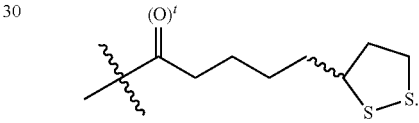

In some embodiments, one Z is

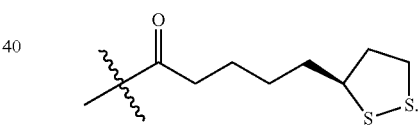

In some embodiments, one Z is

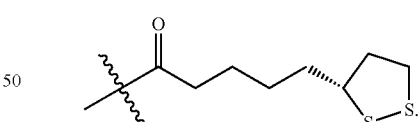

Methods for Using Lipoic Acid Acylated Salicylate Derivatives

The invention also includes methods for treating diseases that have inflammation as an underlying component of their etiology such as metabolic disease, atherosclerosis, coronary heart disease, Type 2 diabetes, diabetic nephropathy, diabetic neuropathy, diabetic retinopathy, metabolic syndrome and cardiovascular disease. Diseases that inflammation as a part of their underlying etiology such as cystic fibrosis, Alzheimer's disease and muscular dystrophy.

In one embodiment, the method comprises contacting a cell with a lipoic acid acylated salicylate derivative in an amount sufficient to decrease the release of TNFα, MCP-1, VCAM-1.

Also provided in the invention is a method for inhibiting, preventing, or treating a metabolic disease, or symptoms of a metabolic disease, in a subject. Examples of such disorders include, but are not limited to atherosclerosis, hypertension, heart failure, stable angina, coronary heart disease, acute myocardial infarction, secondary prevention of myocardial infarction, cardiomyopathy, endocarditis, type 2 diabetes, insulin resistance, impaired glucose tolerance, chronic kidney disease, intermittent claudication, hyperphosphatemia, carotid atherosclerosis, peripheral arterial disease, diabetic nephropathy, acute coronary syndrome (ACS), non-alcoholic fatty liver disease, arterial occlusive diseases, cerebral arteriosclerosis, cerebrovascular disorders, myocardial ischemia, and diabetic autonomic neuropathy.

In some embodiments, the subject is administered an effective amount of a lipoic acid acylated salicylate derivative to treat an inflammatory central nervous system disorder such as Alzheimer's disease.

The invention also includes pharmaceutical compositions useful for treating or preventing a metabolic disease, or for inhibiting a metabolic disease, or more than one of these activities. The compositions can be suitable for internal use and comprise an effective amount of a lipoic acid acylated salicylate derivative and a pharmaceutically acceptable carrier. The lipoic acid acylated salicylate derivatives are especially useful in that they demonstrate very low peripheral toxicity or no peripheral toxicity.

The lipoic acid acylated salicylate derivatives can each be administered in amounts that are sufficient to treat or prevent a metabolic disease or prevent the development thereof in subjects.

Administration of the lipoic acid acylated salicylate derivatives can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a lipoic acid acylated salicylate derivative and a pharmaceutically acceptable carrier, such as: a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the lipoic acid acylated salicylate derivative is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the lipoic acid acylated salicylate derivatives.

The lipoic acid acylated salicylate derivatives can be also formulated as a suppository that can be prepared from fatty emulsions or suspensions using polyalkylene glycols such as propylene glycol, as the carrier.

The lipoic acid acylated salicylate derivatives can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564, the contents of which are herein incorporated by reference in their entirety.

Lipoic acid acylated salicylate derivatives can also be delivered by the use of monoclonal antibodies as individual carriers to which the lipoic acid acylated salicylate derivatives are coupled. The lipoic acid acylated salicylate derivatives can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the lipoic acid acylated salicylate derivatives can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, lipoic acid acylated salicylate derivatives are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 1% to about 90%, from about 10% to about 80%, or from about 20% to about 70% of the lipoic acid acylated salicylate derivative by weight or volume.

The dosage regimen utilizing the lipoic acid acylated salicylate derivative is selected in accordance with a variety of factors including type, species, age, weight, sex and medical condition of the patient; the severity of the condition to be treated; the route of administration; the renal or hepatic function of the patient; and the particular lipoic acid acylated salicylate derivative employed. A physician or veterinarian of ordinary skill in the art can readily determine and prescribe the effective amount of the drug required to prevent, counter or arrest the progress of the condition.

Effective dosage amounts of the present invention, when used for the indicated effects, range from about 20 mg to about 2,000 mg of the lipoic acid acylated salicylate derivative per day. Compositions for in vivo or in vitro use can contain about 20, 50, 75, 100, 150, 250, 500, 750, 1,000, 1,250, 2,500, 3,500, or 5,000 mg of the lipoic acid acylated salicylate derivative. In one embodiment, the compositions are in the form of a tablet that can be scored. Effective plasma levels of the lipoic acid acylated salicylate derivative can range from about 0.002 mg to about 100 mg per kg of body weight per day. Appropriate dosages of the lipoic acid acylated salicylate derivatives can be determined as set forth in Goodman, L. S.; Gilman, A. *The Pharmacological Basis of Therapeutics,* 5th ed.; MacMillan: New York, 1975, pp. 201-226.

Lipoic acid acylated salicylate derivatives can be administered in a single daily dose, or the total daily dosage can be administered in divided doses of two, three or four times daily. Furthermore, lipoic acid acylated salicylate derivatives can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of the lipoic acid acylated salicylate derivative ranges from about 0.1% to about 15%, w/w or w/v.

METHODS OF MAKING

Methods for Making the Lipoic Acid Acetylated Salicylate Derivatives

Examples of synthetic pathways useful for making lipoic acid acylated salicylate derivatives of Formula I are set forth in the Examples below and generalized in Schemes 1 through 10.

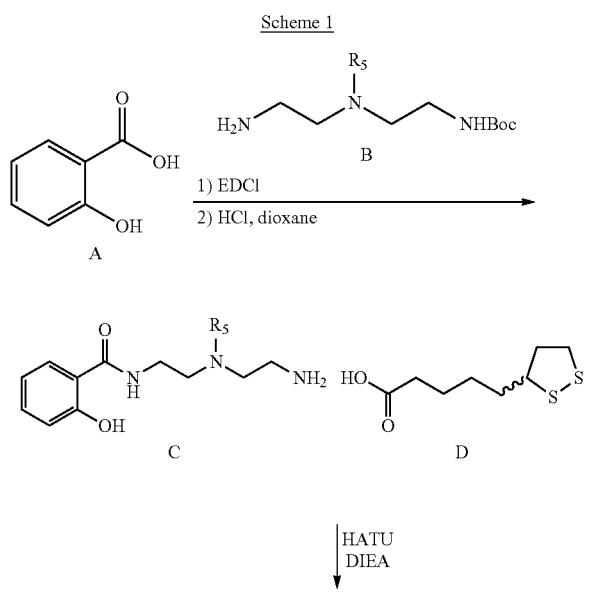

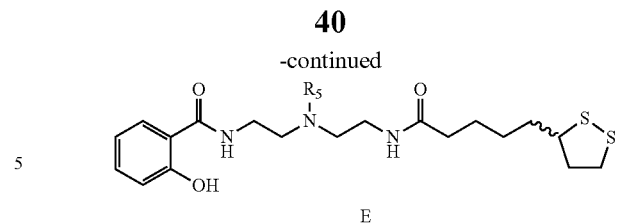

wherein $R_5$ is as defined above.

The mono-BOC protected amine of the Formula B can be obtained from commercial sources or prepared according to the procedures outlined in Krapcho et al. *Synthetic Commun.* 1990, 20, 2559-2564. Compound A can be amidated with the amine B using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound C. Activation of compound C with a coupling agent such as HATU in the presence of an amine such as DIEA followed by addition of lipoic acid D affords compounds of the formula E.

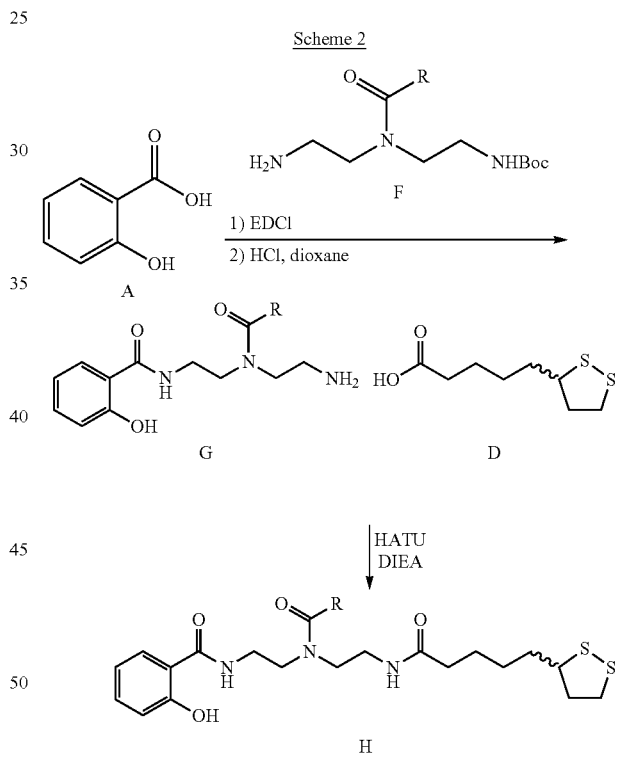

wherein R is as defined above.

The acylated amine of the Formula F can be prepared using the procedures outlined in Andruszkiewicz et al. *Synthetic Commun.* 2008, 38, 905-913. Compound A can be amidated with the amine F using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound G. Activation of compound G with a coupling agent such as HATU in the presence of an amine such as DIEA followed by addition of lipoic acid D affords compounds of the formula H.

Scheme 3

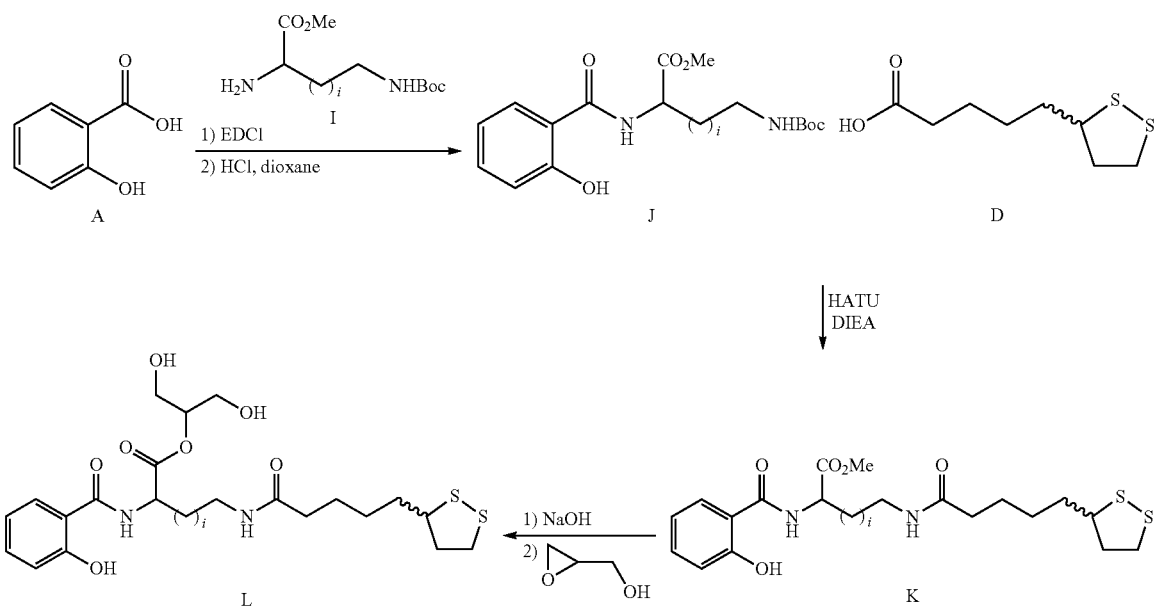

Compound A can be amidated with the corresponding amine I (where i=0, 1, 2 or 3) using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound J. Activation of compound J with a coupling agent such as HATU in the presence of an amine such as DIEA followed by addition of lipoic acid D affords compounds of the formula K. Hydrolysis of the ester under basic conditions such as NaOH or LiOH produces the corresponding acid, which can be coupled with glycidol to afford compounds of the Formula L.

Scheme 4

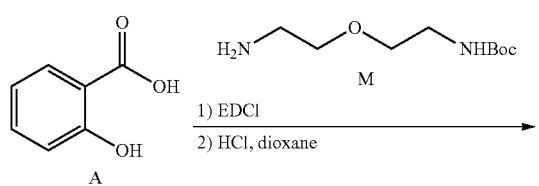

-continued

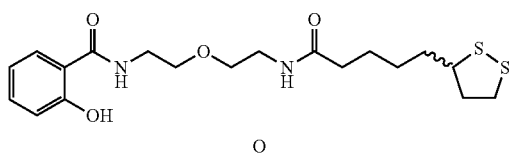

The amine M can be prepared according to the procedures outlined in Dahan et al. *J. Org. Chem.* 2007, 72, 2289-2296. Compound A can be coupled with the amine M using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound N. Activation of compound N with a coupling agent such as HATU in the presence of an amine such as DIEA followed by addition of lipoic acid D affords compounds of the formula O.

Scheme 5

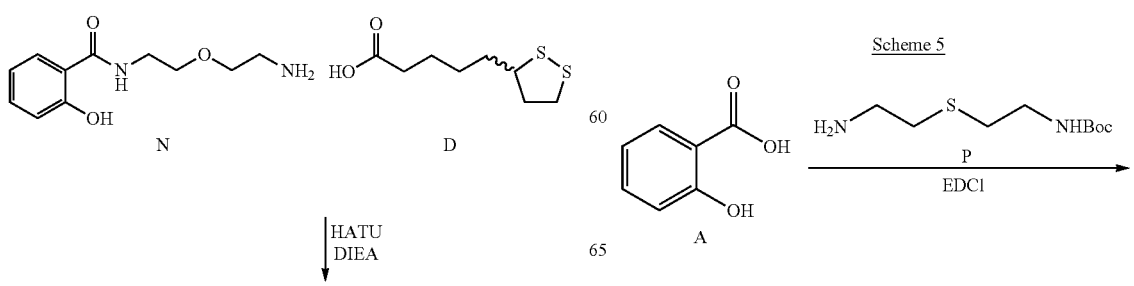

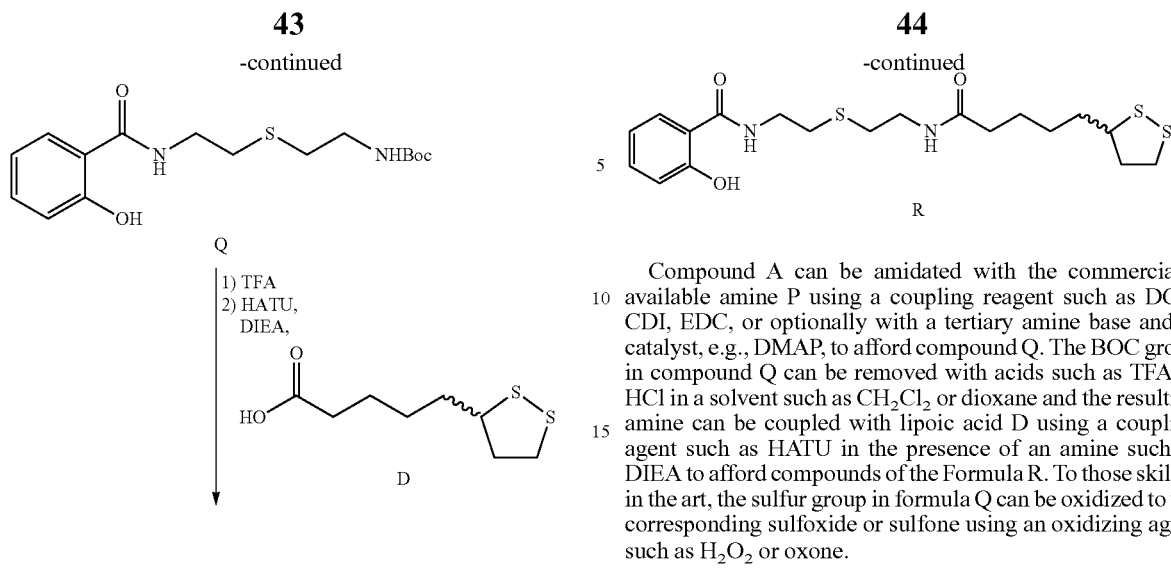

Compound A can be amidated with the commercially available amine P using a coupling reagent such as DCC, CDI, EDC, or optionally with a tertiary amine base and/or catalyst, e.g., DMAP, to afford compound Q. The BOC group in compound Q can be removed with acids such as TFA or HCl in a solvent such as $CH_2Cl_2$ or dioxane and the resulting amine can be coupled with lipoic acid D using a coupling agent such as HATU in the presence of an amine such as DIEA to afford compounds of the Formula R. To those skilled in the art, the sulfur group in formula Q can be oxidized to the corresponding sulfoxide or sulfone using an oxidizing agent such as $H_2O_2$ or oxone.

Scheme 6

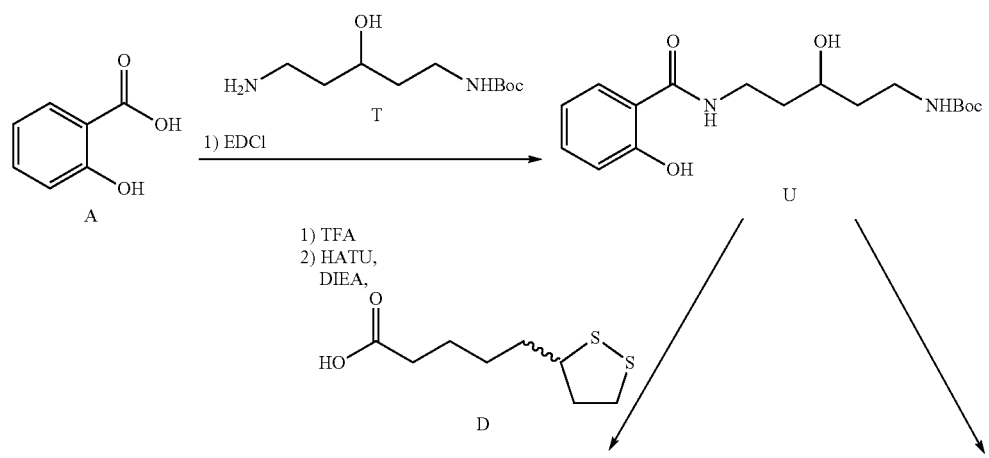

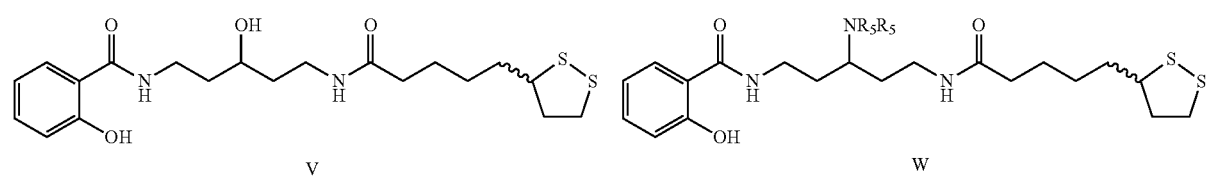

wherein $R_5$ is as defined above.

The amine T can be prepared from the commercially available diamine according to the procedures outlined in Dahan et al. *J. Org. Chem.* 2007, 72, 2289-2296. Compound A can be amidated with the amine T using a coupling reagent such as DCC, CDI, EDC, or optionally with a tertiary amine base and/or catalyst, e.g., DMAP, to afford compound U. The BOC group of compound U can be removed with acids such as TFA or HCl in a solvent such as CH$_2$Cl$_2$ or dioxane and the resulting amine can be coupled with lipoic acid D using HATU in the presence of an amine such as DIEA to afford compounds of the Formula V. To those skilled in the art, the hydroxyl group in compound U can be further acylated or converted to an amino group by standard mesylation chemistry followed by displacement with sodium azide and hydrogenation over a catalyst such as Pd/C. The amine can be further acylated or alkylated, followed by the removal of the BOC group. The resulting amine can be coupled with lipoic acid D to afford compounds of the formula W.

Scheme 7

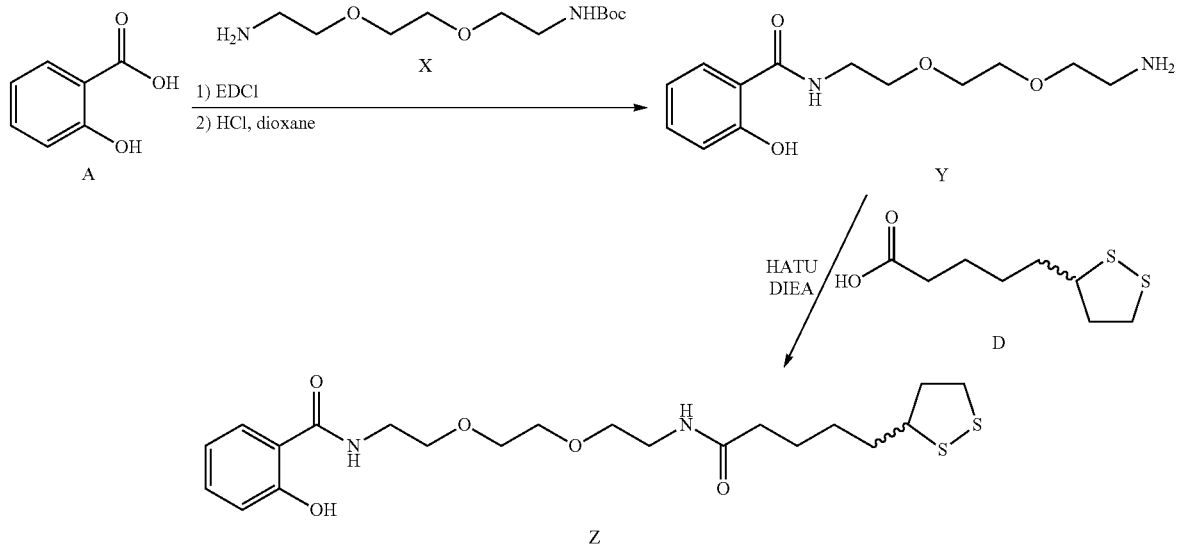

Compound A can be amidated with the commercially available amine X using a coupling reagent such as DCC, CDI, EDC, optionally with a tertiary amine base and/or catalyst, e.g., DMAP to afford compound Y. The BOC group in compound Y can be removed with acids such as TFA or HCl in a solvent such as CH$_2$Cl$_2$ or dioxane. The resulting amine can be coupled with lipoic acid D using a coupling agent such as HATU in the presence of an amine such as DIEA to afford compounds of the Formula Z.

Scheme 8

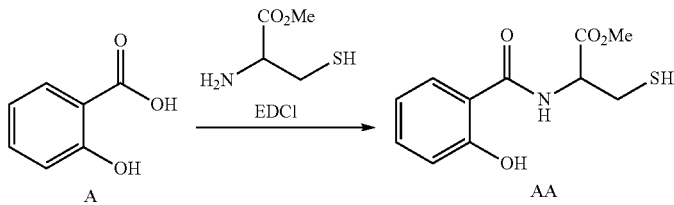

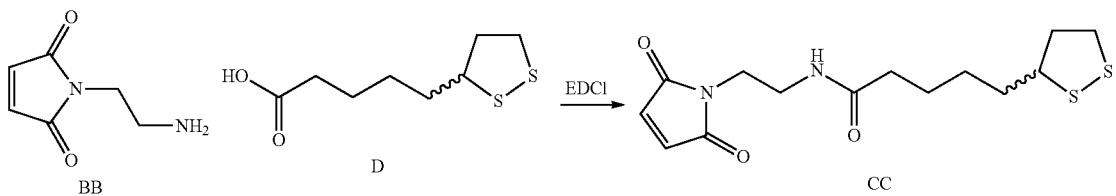

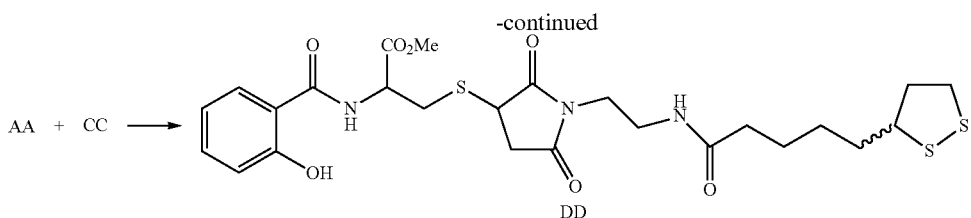

Compound A can be amidated with the commercially available cysteine methyl ester using a coupling reagent such as DCC, CDI, EDC, or optionally with a tertiary amine base and/or catalyst, e.g., DMAP, to afford compound AA. The commercially available maleimide derivative BB can be coupled with lipoic acid D using a coupling agent such as HATU or EDCI to afford compounds of the Formula CC. Compound AA can be coupled to compounds of the Formula CC in a solvent such as acetonitrile to afford compounds of the Formula DD.

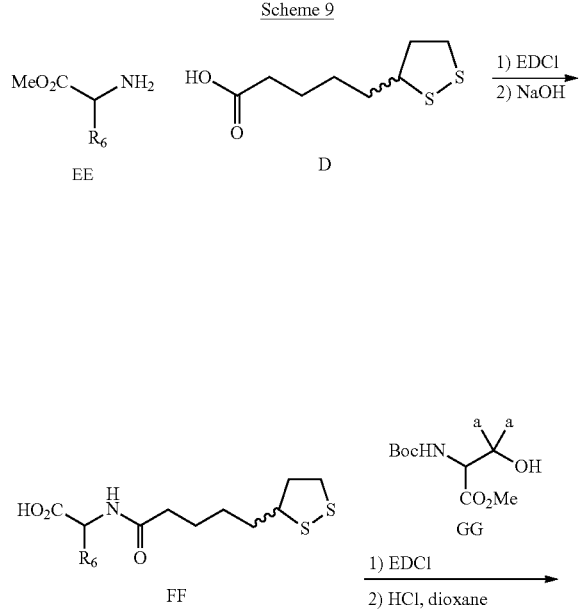

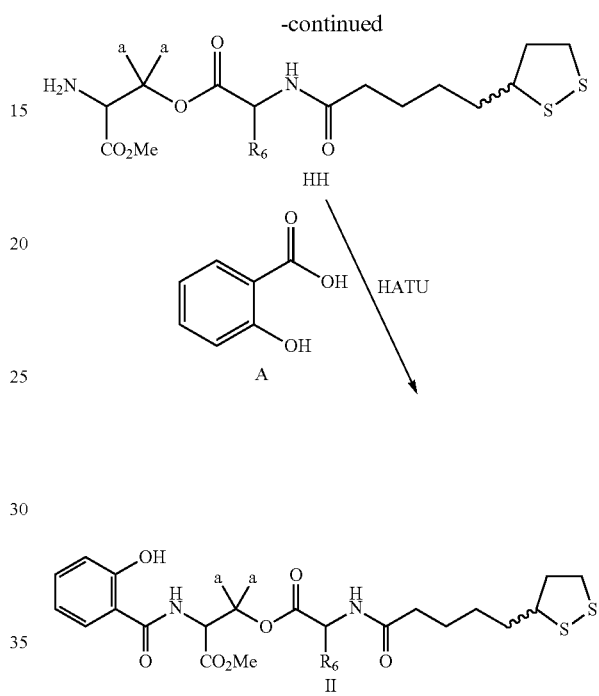

wherein a and $R_6$ are as defined above.

The commercially available amino acid esters EE can be coupled with lipoic acid D using a coupling agent such as EDCI or HATU, followed by alkaline hydrolysis of the methyl ester to afford compounds of the Formula FF. Compounds of the Formula FF can be coupled with the commercially available BOC-amino acid derivatives GG using a coupling agent such as EDCI or HATU. The BOC group can be removed by treatment with acids such as TFA or HCl in a solvent such as $CH_2Cl_2$ or dioxane to afford compounds of the Formula HH which can then be coupled with compound A to afford compounds of the Formula II.

Scheme 10

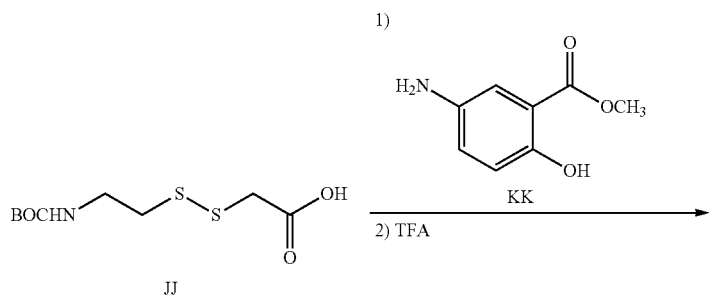

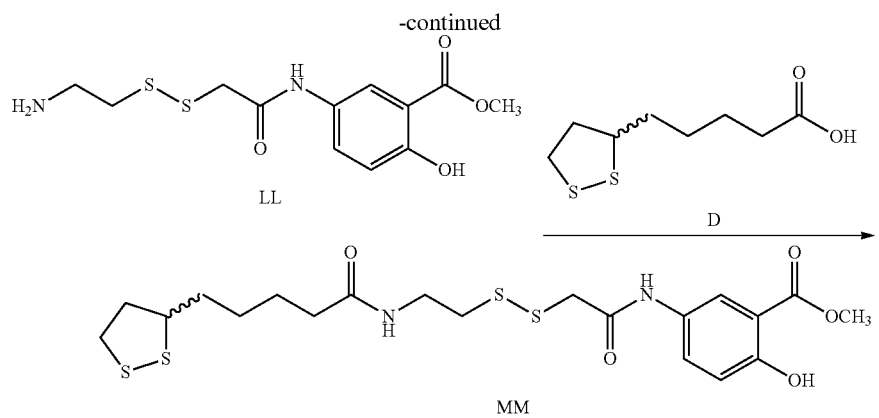

The acid JJ can be prepared using literature procedures (Méry, J. et al. *Peptide Res.* 1992, 5 (4), 233-240). Compound JJ can be coupled with aniline KK using a suitable coupling agent such as DCC, CDI, EDC, or optionally with a tertiary amine base and/or catalyst, e.g., DMAP, which, after deprotection with an acid such as TFA or HCl provides Compound LL. Compound LL can be coupled with Lipoic acid D using a suitable coupling agent such as HATU, CDI, EDC, or optionally with a tertiary amine base and/or catalyst, e.g., DMAP, to produce Compound MM. Compound MM can be hydrolyzed to the free benzoic acid analog using standard basic saponification methods such as NaOH or LiOH.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Effect of Lipoic Acid Acylated Salicylate Derivatives on NFκB Activity in Raw Macrophages Both lipoic acid (DeMarco, V. G. et al. *Free Radical Res.* 2004, 38 (7), 675-682) and salicylate have been shown to inhibit NFκB activity in RAW macrophages challenged with LPS.

The method described is used to measure the effects of lipoic acid in RAW macrophages, with measurement of nitrite and TNFα accumulation accomplished using RAW 264.7 cells cultured in 96-well plates (Kiemer, A. K. et al. *Immunol. Cell Biol.* 2002, 80, 550-557). Cells were treated with bacterial LPS (*E. coli*, serotype 055:B5, 1 μg/mL) in the presence or absence of various concentrations of lipoic acid (5-500 μg/mL). Alpha-Lipoic acid was first dissolved in ethyl alcohol (EtOH) and further diluted with medium. Final EtOH concentrations on the cells were less than or equal to 0.1% and were shown not to interfere with the assay. After 20 h, the concentration of nitrite, a stable metabolite of NO, was measured in the culture supernatant by the Griess assay as described previously. In a different set of experiments the NO donor sodium nitroprusside (SNP, 1 mg/mL) was added to the cells in the presence or absence of lipoic acid and nitrite accumulation was measured after 1.5, 2.5 and 4.5 h.

Tumor necrosis factor-α was measured after 4 h of LPS treatment by L929 bioassay as described in Kiemer, A. K. et al. *Immunol. Cell Biol.* 2002, 80, 550-557. This assay is based upon quantification of the cytotoxic activity of TNFα on L929 cells in the presence of actinomycin D. Briefly, L929 cells were seeded at a density of $4 \times 10^4$ cells per well into a 96-well microtiter plate. Following incubation for 24 h at 37° C. in a humidified atmosphere with 5% $CO_2$, the medium in the wells was replaced with fresh medium containing actinomycin D (1 μg/mL). After 1 h of preincubation with actinomycin D serial dilutions of supernatants from KC untreated or treated with lipoic acid in the presence or absence of LPS for 4 h were added. For quantification of TNFα production, a standard curve was prepared by the addition of recombinant TNFα (0.75-50. picomol/L) to the cells. The plates were then incubated for an additional 24 h at 37° C. followed by incubation with 3-(4,5-dimethylthiazol-2-yl)-2,5-diphenyl tetrazolium bromide (MTT) (0.5 mg/mL) for 1 h, solubilization in DMSO, and spectrophotometric measurement at 550 nm. In some experiments positive samples, in which TNFα was neutralized with TNFα-antiserum (Sepharose-A purified goat antiserum against mouse TNFα provided by Thomas Hartung, University of Konstanz, Germany), were assayed in parallel.

Example 2

Effect of Lipoic Acid Acylated Salicylate Derivatives on the Target Gene Hmox1 in Raw Macrophages RAW264.7 macrophages are seeded at a density of 100,000 cells/well in a 96-well plate in DMEM supplemented with 10% FBS and Penn/strep. 16 hours later, medium is aspirated and replaced with 90 uL/well of serum-free DMEM. A lipoic acid acylated salicylate conjugate, DHA and EPA are brought up in 100% EtOH to a concentration of 100 mM and then diluted 1:100 in 100% FBS for a 20× stock solution consisting of 1 mM compound and 1% EtOH. The lipoic acid acylated salicylate conjugate 20× stock solutions are diluted 1:2 in FBS supplemented with 1% EtOH for a 500 uM 10× stock solution, whereas equal volumes of the DHA and EPA 20× stock solutions are mixed to create a 10× stock solution containing 500 μM each of DHA and EPA. The 10× stock solutions are then serially diluted 1:2 in FBS supplemented with 1% EtOH and 10 μL of each dilution is added to the RAW246.7 cells to generate final concentrations of 50, 25, 12.5, 6.25, 3.12 and 1.6 μM. The compounds are allowed to pre-incubate for 2 hours before stimulation of 100 ng/ml LPS (10 μL of 1 μg/ml LPS is added to each well). Following 3 hours of LPS stimulation, cells are washed once in 1×PBS, aspirated dry, and flash frozen in liquid nitrogen. RNA is then isolated and converted to cDNA using the Cells to cDNA kit (Ambion) according to the manufacturer's protocol. Transcript levels are then measured using ABI Taqman primer/probe assay kits, normalized to GAPDH using the deltaCt method, and the data expressed relative to vehicle only control.

Example 3

TNFα Release Assay in RAW 264.7 Macrophages

The purpose of this assay is to measure the ability of small molecules to inhibit the secretion of TNFα in cultured macrophages stimulated with lipopolysaccharide (LPS). Treatment of macrophages with LPS activates inflammatory cytokine pathways primarily through the TLR4-NFκB signaling axis. Compounds of the invention inhibit the transcriptional activation of NFκB and thus decrease the production and release of TNFα. Dexamethasone, a potent agonist of the glucocorticoid receptor is used a positive control for inhibition of TNFα release.

Day 1: Seed RAW 264.7 macrophages into 96 well culture plates. Remove culture media from RAW 264.7 cell growing in a 75 $mm^2$ tissue culture flask (cells should be at ~70% confluence) and add 10 mL of warmed complete growth media (DMEM+10% FBS+1×pen/step). The cells are scraped into suspension using a sterile plate scraper and homogenized by pipetting up and down with a 10 mL serological pipette. The cell concentration is determined using a clinical hematoctyometer. Cells are then diluted to 150,000 cells per mL into growth media. The diluted cells are then transferred to a sterile reagent reservoir and 100 μl of cell suspension is pipetted into each well of a 96 well culture plate using a multichannel pipette (15,000 cells/well). Plates are then incubated at 37° C. under normal tissue culture growth conditions (37° C., humidified $CO_2$ chamber).

Day 2: The test compound sample plate is prepared. Test compounds are prepared in growth media. Compounds are delivered to media from 1000× stocks in 100% DMSO (e.g. for a 10 μM final concentration of test compound, deliver 2 μl of 10 mM test compound to 2 mL of media). At least 150 μl of 1×compound in media is added to 96 well sample plate. The perimeter wells of the 96 well plate are not used to avoid edge effects. Twelve sample wells are prepared with media plus 0.1% DMSO (these samples will serve as the vehicle controls; LPS-stimulated and non-stimulated; 10 μM dexamethasone is used as a positive control). Culture plates are then returned to the growth incubator for 2 hours. Cells are stimulated afterwards by adding 25 μl of 50 ng/mL LPS is added to every well (except the 6 unstimulated vehicle control wells: final concentration of 10 ng/mL LPS. Plates are returned to growth incubator for 3 hours. Afterwards, 100 μl of media supernatant is removed and transferred to a 96 well v-bottom sample plate. The media supernatant plate is centrifuged for 5 minutes at 1,000 rpm in a swing-bucket centrifuge, pelleting any cellular debris that may remain in supernatant. 80 μl of supernatant is removed from sample plate and transferred to a fresh v-bottom 96 well plate. Cell viability is measured using Celltiter-glo kit. By measuring cell viability, a given compound's effects on TNFα secretion can determine whether effects are due to cytotoxicity or to true inhibition of inflammatory signaling. Add 100 μl of Celltiter-glo reagent to each well of the cell culture plate and afterwards measure the luminescence signal (CPS) of the plate using the Victor 5 plate reader (0.3 second read; 60 second plate shaking prior to read). Cell viability of a given compound at a given concentration is computed as follows:

Cell viability=CPS Sample/(Average CPS unstimulated controls)*100

Use 20 μl of media supernatant per well for TNFα ELISA. Follow Invitrogen/Biosource manufacture's protocol for the mouse TNFα ELISA. Chromogen development is typically conducted for 20-30 minutes as described in the manufacturer's protocol. After addition of stop solution, measure OD 450 nm using the Victor 5 plate reader (0.1 second/well scan). Determine the TNFα secretion percent of control. The following formula is used to determine the TNFα secretion percent of control:

$$\frac{100 \times (OD\ 450\ nm\ Sample\ X) - (\text{Average } OD\ 450\ nm\ \text{unstimulated vehicle controls})}{(\text{Average } OD\ 450\ nm\ LPS\ \text{stimulated vehicle controls}) - (\text{Average } OD\ 450\ nm\ \text{unstimulated vehicle controls})}$$

For each test compound, TNFα secretion percent of control can be plotted as a function of compound concentration using a four parameter dose-response curve fit equation (XLFIT Model #205):

fit=$(A+((B-A)/(1+((C/x)\hat{}D))))$ inv=$(C/((((B-A)/(y-A))-1)\hat{}(1/D)))$ res=$(y-\text{fit})$

Compounds

The following non-limiting compound examples serve to illustrate further embodiments of the lipoic acid acylated salicylate derivatives. It is to be understood that any embodiments listed in the Examples section are embodiments of the lipoic acid acylated salicylate derivatives and, as such, are suitable for use in the methods and compositions described above.

Example 4

Preparation of (S)—N-(2-(5-(1,2-dithiolan-3-yl)pentanamido)ethyl)-2-hydroxybenzamide (I-1)

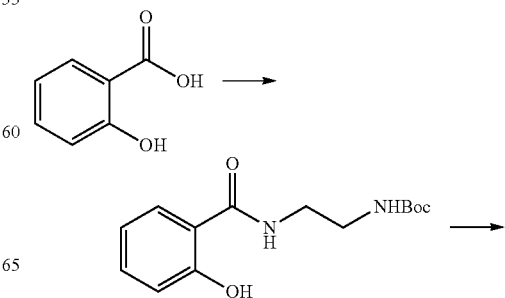

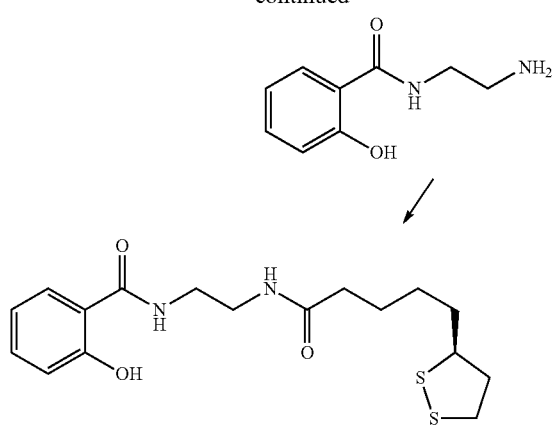

Salicylic acid (4.3 g, 0.0312 mol) was taken up in 60 mL of CH$_2$Cl$_2$ along with tert-butyl 2-aminoethylcarbamate (5.0 g, 0.0312 mol) and EDC (6.6 g, 0.0343 mol). The resulting reaction mixture was stirred at room temperature for 8 h and then quenched with saturated aqueous NaHCO$_3$. The organic layer was separated and washed with brine, dried (Na$_2$SO$_4$) and concentrated under reduced pressure. Purification by chromatography (1:1 pentane/EtOAc) afforded 5.7 g of tert-butyl 2-(2-hydroxybenzamido)ethylcarbamate (65%). tert-Butyl 2-(2-hydroxybenzamido)ethylcarbamate (650 mg, 2.31 mmol) was taken up in 4 mL of 4 N HCl in dioxane and allowed to stir at room temperature for 2 h. The reaction mixture was diluted with EtOAc and concentrated under reduced pressure to afford the HCl salt of N-(2-aminoethyl)-2-hydroxybenzamide. This material was taken up in DMF (15 mL) along with (R)-α-lipoic acid (TCI, 478 mg, 2.31 mmol) along with EDC (443 mg, 2.54 mmol) and DIEA (1.2 mL, 6.93 mmol). The resulting reaction mixture was stirred at room temperature for 4 h and then diluted with EtOAc (60 mL). The organic layer was washed with water (4×5 mL), brine, dried (Na$_2$SO$_4$) and concentrated under reduced pressure to afford (S)—N-(2-(5-(1,2-dithiolan-3-yl)pentanamido)ethyl)-2-hydroxybenzamide (420 mg, 49%). Mass calculated for C$_{17}$H$_{24}$N$_2$O$_3$S$_2$: 368.12. found: [M+H]$^+$=369.

Example 5

Preparation of (S)—N-(2-(2-(2-(5-(1,2-dithiolan-3-yl)pentanamido)ethyl)disulfanypethyl)-2-hydroxybenzamide (I-2)

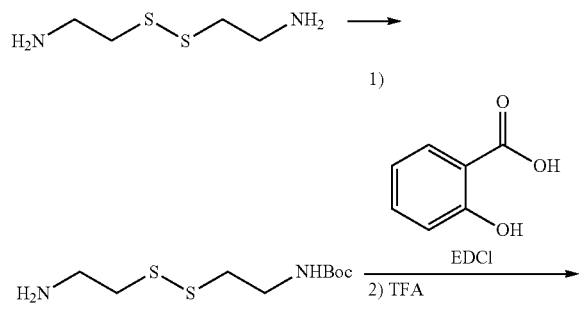

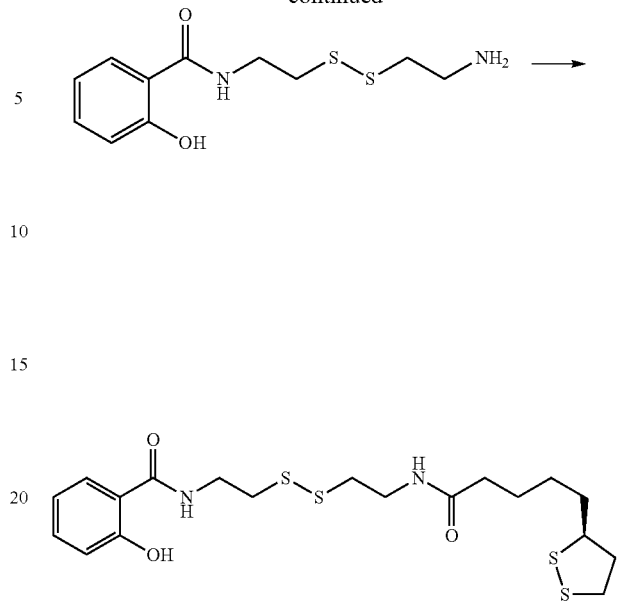

Cystamine dihydrochloride (1.0 g, 4.44 mmol) was dissolved in MeOH (50 mL). Triethylamine (1.85 mL, 3 eq) was added at room temperature, followed by dropwise addition of Boc$_2$O (0.97 g, 4.44 mmol) as a solution in 5 mL of MeOH The resulting reaction mixture was stirred at room temperature for 3 h. It was then concentrated under reduced pressure and the resulting residue was taken up in 1M NaH$_2$PO$_4$ (20 mL). The aqueous layer was washed with 10 mL of a 1:1 solution of pentane/EtOAc, basified to pH 9 with 1M NaOH, and extracted with EtOAc. The combined organic layers were washed with brine, dried over Na$_2$SO$_4$ and concentrated under reduced pressure to afford tert-butyl 2-(2-(2-aminoethyl)disulfanyl)ethylcarbamate (500 mg, 44%).

tert-Butyl 2-(2-(2-aminoethyl)disulfanyl)ethylcarbamate (500 mg, 1.98 mmol) was taken up in CH$_2$Cl$_2$ (20 mL) along with salicylic acid (273 mg, 1.98 mmol) and EDCI (693 mmol, 2.2 mmol). The resulting reaction mixture was stirred at room temperature for 18 h. It was then diluted with CH$_2$Cl$_2$, washed with saturated aqueous NaHCO$_3$, brine, dried over Na$_2$SO$_4$ and concentrated under reduced pressure. Purification by chromatography (40% EtOAc, 60% pentane) afforded tert-butyl 2-(2-(2-(2-hydroxybenzamido)ethyl)disulfanyl)ethylcarbamate (400 mg, 54%). Mass calculated for C$_{16}$H$_{24}$N$_2$O$_4$S$_2$: 372.12. found: [M+H]$^+$=373.

tert-Butyl 2-(2-(2-hydroxybenzamido)ethyl)disulfanyl)ethylcarbamate (120 mg, 0.322 mmol) was taken up in 3 mL of 4 N HCl in dioxane and allowed to stand at room temperature for 1 h. The reaction mixture was concentrated under reduced pressure to afford the HCl salt of N-(2-(2-(2-aminoethyl)disulfanyl)ethyl)-2-hydroxybenzamide.

The HCl salt of N-(2-(2-(2-aminoethyl)-disulfanyl)-ethyl)-2-hydroxybenzamide (0.322 mmol) was taken up in DMF (5 mL) along with (R)-α-lipoic acid (TCI, 66 mg, 0.322 mmol) HATU (134 mg, 0.354 mmol) and DIEA (170 μL, 0.97 mmol). The resulting reaction mixture was stirred at room temperature for 4 h. It was then diluted with EtOAc (30 mL) and washed successively with water (3×5 mL) and brine. The organic layer was dried over Na$_2$SO$_4$ and concentrated under reduced pressure. Purification by chromatography (CH$_2$Cl$_2$) afforded (S)—N-(2-(2-(2-(5-(1,2-dithiolan-3-yl)pentanamido)ethyl)disulfanyl)ethyl)-2-hydroxybenzamide (35 mg, 24%). Mass calculated for $C_{19}H_{28}N_2O_3S_4$: 460.1. found: $[M+H]^+=461$.

Example 6

Preparation of (S)—N-(2-(2-(5-(1,2-dithiolan-3-yl)pentanamido)ethoxy)ethyl)-2-hydroxybenzamide (I-3)

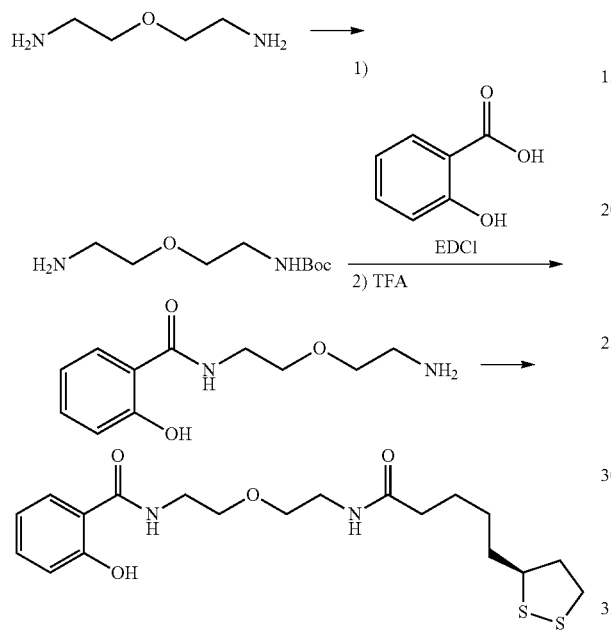

In a typical run, sodium hydroxide (400 mg, 10 mmol) was dissolved in MeOH (70 mL) and 2-(2-aminoethoxy)-ethanamine dihydrochloride (1.0 g, 5.65 mmol) was added. The resulting reaction mixture was stirred at room temperature for 30 minutes. A solution containing Boc$_2$O (740 mg, 3.40 mmol) in THF (15 mL) was then added dropwise, at room temperature, over a period of 15 minutes. The resulting reaction mixture was stirred at room temperature for 18 h and then concentrated under reduced pressure. The resulting residue was taken up in CH$_2$Cl$_2$ (200 mL) and stirred vigorously at room temperature for 4 h. The mixture was filtered and the filtrate was concentrated under reduced pressure to afford tert-butyl 2-(2-aminoethoxy)ethylcarbamate (850 mg, 74%).

tert-Butyl 2-(2-aminoethoxy)ethylcarbamate was then taken up in CH$_2$Cl$_2$ (20 mL) along with salicylic acid (576 mg, 4.17 mmol) and EDCI (905 mg. 4.72 mmol). The resulting reaction mixture was stirred at room temperature for 18 h. It was then diluted with CH$_2$Cl$_2$ (20 mL), washed with saturated aqueous NaHCO$_3$, brine, dried over Na$_2$SO$_4$ and concentrated under reduced pressure. The resulting residue was purified by chromatography (9:1 CH$_2$Cl$_2$/MeOH) to afford tert-butyl 2-(2-(2-hydroxybenzamido)ethoxy)ethylcarbamate (450 mg, 33%). Mass calculated for $C_{16}H_{24}N_2O_5$: 324.17. found: $[M+H]^+=325$.

tert-Butyl 2-(2-(2-hydroxybenzamido)ethoxy)ethylcarbamate (220 mg, 0.68 mmol) was taken up in 4 mL of 4 N HCl in dioxane and allowed to stand at room temperature for 1 h and then concentrated under reduced pressure to afford the HCl salto of N-(2-(2-aminoethoxy)ethyl)-2-hydroxybenzamide. This material was then taken up in DMF (5 mL) along with (R)-α-lipoic acid (TCI, 140 mg, 0.68 mmol) HATU (285 mg, 0.75 mmol) and DIEA (360 µL, 2.0 mmol). The resulting reaction mixture was stirred at room temperature for 2 h. It was then diluted with EtOAc (30 mL) and washed with water (3×5 mL) and brine. The organic layer was dried over Na$_2$SO$_4$ and concentrated under reduced pressure. Purification by chromatography (gradient elution from CH$_2$Cl$_2$ to 9:1 CH$_2$Cl$_2$/MeOH) afforded (S)—N-(2-(2-(5-(1,2-dithiolan-3-yl)pentanamido)ethoxy)ethyl)-2-hydroxybenzamide (70 mg, 25%). Mass calculated for $C_{19}H_{28}N_2O_4S_2$: 412.15. found: $[M+H]^+=413$.

Example 7

Preparation of (S)—N-(2-((2-(5-(1,2-dithiolan-3-yl)pentanamido)ethyl)(methyl)amino)ethyl)-2-hydroxybenzamide (I-4)

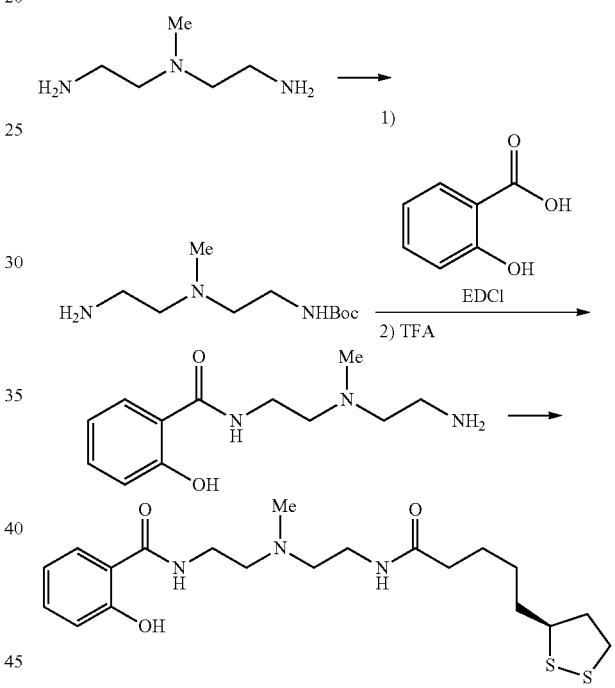

N-1-(2-Aminoethyl)-N1-methylethane-1,2-diamine (5.0 g, 42.7 mmol) was dissolved in CH$_2$Cl$_2$ (100 mL) and cooled to 0° C. A solution of di-tert-butylcarbonate (0.93 g, 4.27 mmol) in CH$_2$Cl$_2$ (10 mL) was then added dropwise at 0° C. over a period of 15 minutes. The resulting reaction mixture was stirred at 0° C. for 30 minutes and then warmed to room temperature. After stirring at room temperature for 2 h, the reaction mixture was diluted with CH$_2$Cl$_2$ (100 mL). The organic layer was washed with brine (3×25 mL), dried over Na$_2$SO$_4$ and concentrated under reduced pressure to afford 1.1 g of tert-butyl 2-((2-aminoethyl)(methyl)amino)ethylcarbamate.

tert-Butyl 2-((2-aminoethyl)(methyl)amino)ethylcarbamate (500 mg, 2.3 mmol) was taken up in CH$_3$CN (10 mL) along with salicylic acid (310 mg, 2.3 mmol) and EDCI (485 mg, 2.53 mmol). The resulting reaction mixture was stirred at room temperature for 18 h and then diluted with EtOAc. The organic layer was washed with saturated aqueous NaHCO$_3$, brine, dried over Na$_2$SO$_4$ and concentrated under reduced pressure. The resulting residue was purified by chromatography (MeOH—CH$_2$Cl$_2$, 5%) to afford tert-butyl 2-((2-(2-hydroxybenzamido)ethyl)(methyl)amino)ethylcarbamate (380 mg, 49%). Mass calculated for C$_{17}$H$_{27}$N$_3$O$_4$: 337.2. found: [M+H]$^+$=338.

tert-Butyl 2-((2-(2-hydroxybenzamido)ethyl)(methyl)amino)ethylcarbamate (135 mg, 0.40 mmol) was taken up in 3 mL of 4 N HCl in dioxane and allowed to stand at room temperature for 1 h. The reaction mixture was concentrated under reduced pressure to afford the HCl salt of N-(2-((2-aminoethyl)(methyl)amino)ethyl)-2-hydroxybenzamide. This material was taken up in DMF (5 mL) along with (R)-α-lipoic acid (TCI, 83 mg, 0.40 mmol) HATU (167 mg, 0.44 mmol) and DIEA (210 µL, 1.2 mmol). The resulting reaction mixture was stirred at room temperature for 2 h. It was then diluted with EtOAc (30 mL) and washed with water (3×5 mL) and brine. The organic layer was dried over Na$_2$SO$_4$ and concentrated under reduced pressure. Purification by chromatography (MeOH—CH$_2$Cl$_2$, 5%) afforded (S)—N-(2-((2-(5-(1,2-dithiolan-3-yl)pentanamido)ethyl)(methyl)amino) ethyl)-2-hydroxybenzamide (110 mg, 65%). Mass calculated for C$_{20}$H$_{31}$N$_3$O$_3$S$_2$: 425.18. found: [M+H]$^+$=426.

Example 8

Preparation of (S)-5-(5-(1,2-dithiolan-3-yl)pentanamido)-2-hydroxybenzoic acid (II-1)

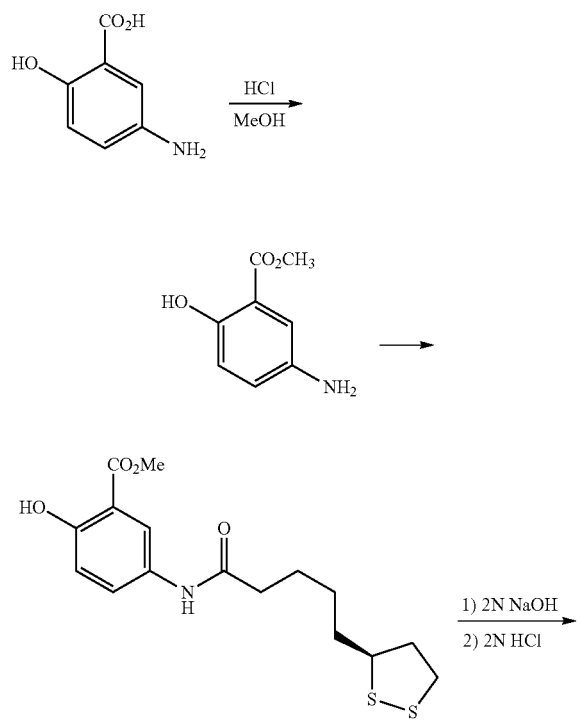

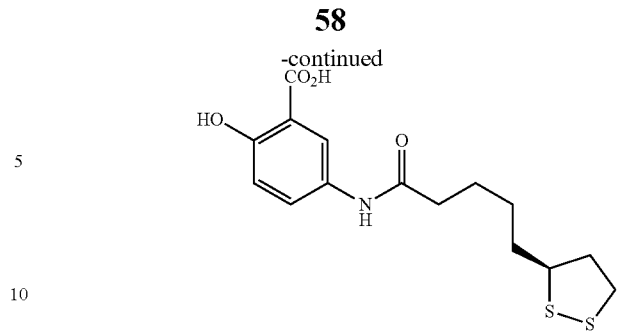

To a solution of saturated HCl in CH$_3$OH (20 mL) at RT was slowly added 5-amino-2-hydroxybenzoic acid (2 g, 13.06 mmol). The resulting mixture was stirred at (RT, 16 h) and then heated (reflux, 24 h). The mixture was cooled and the solvent was removed under reduced pressure. The residue was diluted with EtOAc (50 mL) and washed with saturated aqueous NaHCO$_3$. The organic solution was dried over MgSO$_4$, filtered, concentrated under reduced pressure to afford methyl 5-amino-2-hydroxybenzoate as a pale yellow solid (1.72 g, 78.5%). Mass calculated for C$_8$H$_9$NO$_3$=167.16. found: [M+H]$^+$=168.2.

Methyl 5-amino-2-hydroxybenzoate (500 mg, 2.99 mmol) was taken up in DMF (15 mL) along with (R)-α-lipoic acid (TCI, 618 mg, 2.99 mmol) and EDC (630 mg, 3.3 mmol). The resulting reaction mixture was stirred at room temperature for 18 h and then diluted with EtOAc (60 mL). The organic layer was washed with water (3×10 mL), brine, dried (Na$_2$SO$_4$) and concentrated under reduced pressure. Purification by chromatography (95% CH$_2$Cl$_2$, 5% MeOH) afforded 650 mg of (S)-methyl 5-(5-(1,2-dithiolan-3-yl)pentanamido)-2-hydroxybenzoate (61%). Mass calculated for C$_{16}$H$_{21}$NO$_4$S$_2$=355.09. found: [M+H]$^+$=356.

(S)-methyl 5-(5-(1,2-dithiolan-3-yl)pentanamido)-2-hydroxybenzoate (650 mg, 1.83 mmol) was taken up in 6 mL of THF and NaOH (220 mg, 5.5 mmol) was added as a solution in 6 mL of H$_2$O. The resulting reaction mixture was stirred at room temperature for 8 h and then concentrated under reduced pressure. Enough 1 N HCl was added to the aqueous layer to adjust the pH to 2 and the resulting mixture was extracted with EtOAc (3×20 mL). The combined organic layers were washed with water (2×20 mL), brine, dried (Na$_2$SO$_4$) and concentrated under reduced pressure to afford (S)-5-(5-(1,2-dithiolan-3-yl)pentanamido)-2-hydroxybenzoic acid. Mass calculated for C$_{15}$H$_{19}$NO$_4$S$_2$: 341.08. found: [M+H]$^+$=342.

Example 9

Preparation of 5-(2-(2-(2-(5-(1,2-dithiolan-3-yl)pentanamido)ethyl)disulfanyl)acetamido)-2-hydroxybenzoic acid (II-2)

1)

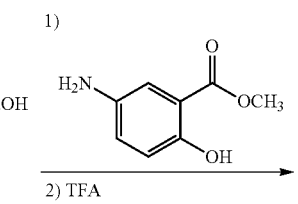

-continued

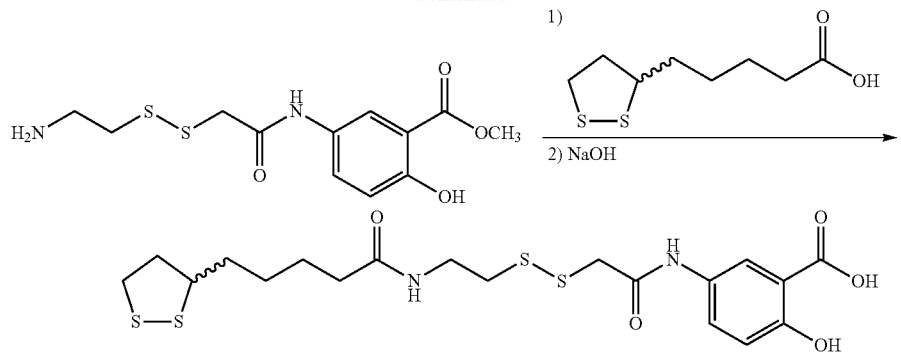

2-(2-(2-(tert-Butoxycarbonyl)ethyl)disulfanyl)acetic acid (1 mmol), which was synthesized according to the procedure outlined in Méry, J. et al. *Peptide Res.* 1992, 5 (4), 233-240, is dissolved in $CH_2Cl_2$ and to this is added EDCI (1.3 mmol) and methyl 5-amino-2-hydroxybenzoate (1 mmol). The reaction is stirred (RT, 4 h) and then partitioned between $CH_2Cl_2$ and water. The aqueous layer is extracted with $CH_2Cl_2$ and the combined organic extracts are washed with water, brine and dried over $MgSO_4$. Solvent evaporation and purification by silica chromatography affords methyl 5-(2-(2-(2-tert-butoxycarbonylaminoethyl)disulfanyl)acetamido)-2-hydroxybenzoate, which is dissolved in $CH_2Cl_2$ and TFA and is stirred (RT, 4 h). Solvent evaporation under reduced pressure affords methyl 5-(2-(2-(2-aminoethyl)disulfanyl)acetamido)-2-hydroxybenzoate, which is then added to a solution of lipoic acid and EDCI. The mixture is stirred (RT, 4 h) and then partitioned between $CH_2Cl_2$ and water. The aqueous layer is extracted with $CH_2Cl_2$ and the combined organic extracts are washed with water, brine and dried over $MgSO_4$. Solvent evaporation under reduced pressure and purification by silica chromatography affords methyl 5-(2-(2-(2-(5-(1,2-dithiolan-3-yl)pentanamido)ethyl)disulfanyl)acetamido)-2-hydroxybenzoate, which is subsequently dissolved in a mixture of THF and water with 5N NaOH. The mixture is stirred (50° C., 3 h) and the volatiles are removed under reduced pressure. The resulting aqueous mixture is extracted with EtOAc, and the combined organic extracts are washed with water, brine and dried over $MgSO_4$. Solvent evaporation under reduced pressure affords 5-(2-(2-(2-(5-(1,2-dithiolan-3-yl)pentanamido)ethyl)disulfanyl)acetamido)-2-hydroxybenzoic acid.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A molecular conjugate comprising a lipoic acid and an ortho salicylate wherein the lipoic acid and the ortho salicylate are conjugated through at least two amides.

2. A compound of Formula I:

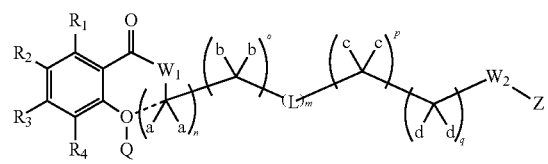

Formula I or a pharmaceutically acceptable salt, hydrate, solvate, enantiomer, or stereoisomer thereof;
wherein
$R_1$, $R_2$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, and —S(O)$_2$$C_1$-$C_3$ alkyl;

$W_1$ and $W_2$ are each independently S, NR, or $W_1$ and $W_2$ can be taken together can form an imidazolidine or piperazine group;

each symbol ----- represents an optional bond, which when present between the phenolic oxygen and the methylene containing substituent a, requires that Q is null, or when present between substituent a and the carbon of the methylene containing substituent a, requires that Q not be null;

each a, b, c, and d is independently —H, -D, —$C_1$-$C_3$ alkyl, —O—$C_1$-$C_3$ alkyl, —C(O)OR, —O—Z, or benzyl, or two of a, b, c, and d can be taken together, along with the single carbon to which they are bound, to form a cycloalkyl or heterocycle;

each n, o, p, and q is independently 0, 1, or 2;
each L is independently —O—, —S—, —S(O)—, —S(O)$_2$—, —S—S—,-($C_1$-$C_6$alkyl)-

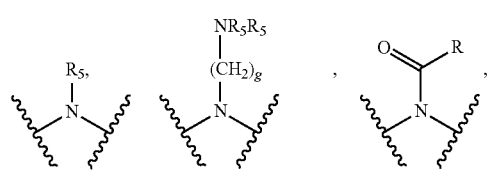

-continued

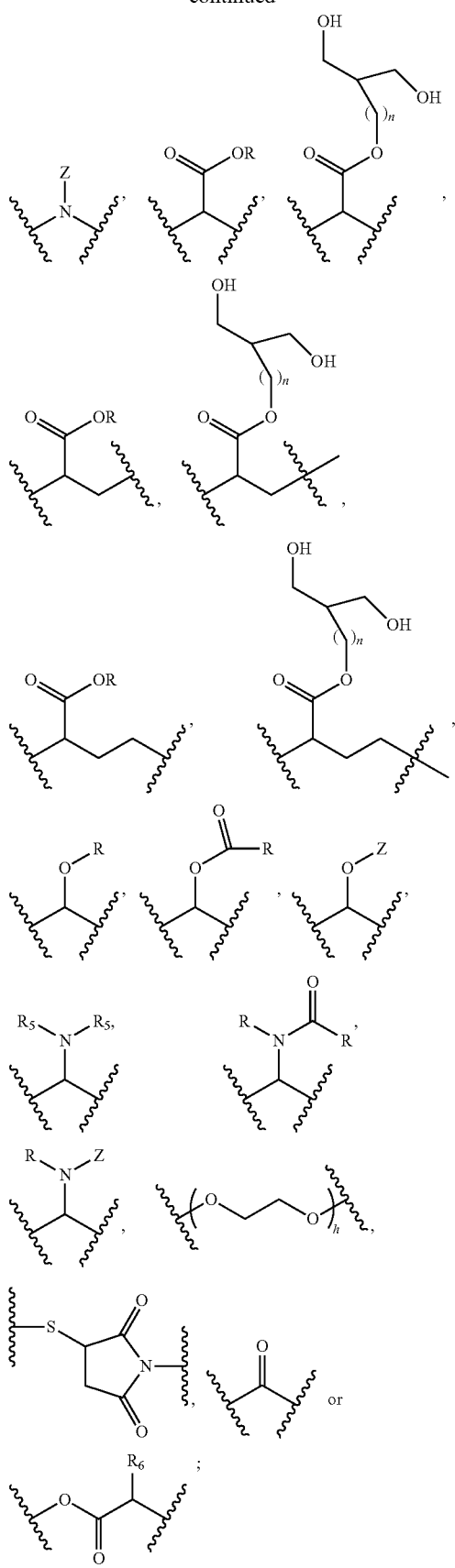

wherein the representation of L is not limited directionally left to right as is depicted, rather either the left side or the right side of L can be bound to the $W_1$ side of the compound of Formula I;

each g is independently 2, 3 or 4;
each h is independently 1, 2, 3 or 4;
m is 0, 1, 2, or 3; if m is more than 1, then L can be the same or different;
each $R_5$ is independently H or $C_1$-$C_6$ alkyl, or both $R_5$ groups, when taken together with the nitrogen to which they are attached, can form a heterocycle;
each $R_6$ is independently e, H, or straight or branched $C_1$-$C_{10}$ alkyl which can be optionally substituted with OH, $NH_2$, $CO_2R$, $CONH_2$, phenyl, $C_6H_4OH$, imidazole or arginine;
each e is independently H or any one of the side chains of the naturally occurring amino acids;
each Z is independently H, or

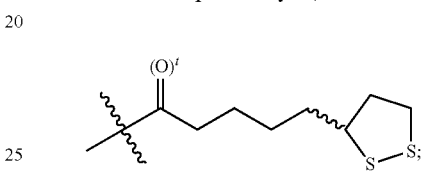

with the proviso that there is at least one

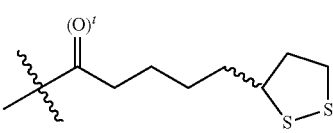

in the compound;
each t is independently 0 or 1;
Q is null, $C(O)CH_3$, Z,

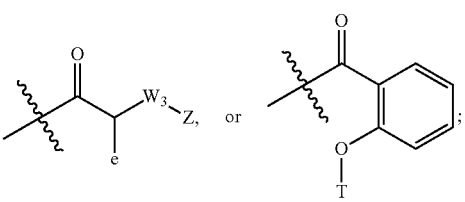

$W_3$ is null, —O—, or —N(R)—;
each R is independently H, —C(O)—$C_1$-$C_3$ alkyl, or straight or branched $C_1$-$C_4$ alkyl optionally substituted with or halogen; and
T is H, C(O)CH3, or Z.

3. The compound of claim 2 selected from a group consisting of
(S)—N-(2-(5-(1,2-dithiolan-3-yl)pentanamido)ethyl)-2-hydroxybenzamide (I-1);
(S)—N-(2-(2-(2-(5-(1,2-dithiolan-3-yl)pentanamido)ethyl)disulfanyl)ethyl)-2-hydroxybenzamide (I-2);
(S)—N-(2-(2-(5-(1,2-dithiolan-3-yl)pentanamido)ethoxy)ethyl)-2-hydroxybenzamide (I-3);
(S)—N-(2-((2-(5-(1,2-dithiolan-3-yl)pentanamido)ethyl)(methyl)amino)ethyl)-2-hydroxybenzamide (I-4);
6-(5-(1,2-dithiolan-3-yl)pentanamido)-2-(2-hydroxybenzamido)hexanoic acid (I-8);

3-hydroxy-2-(hydroxymethyl)propyl 6-(5-(1,2-dithiolan-3-yl)pentanamido)-2-(2-hydroxybenzamido)hexanoate (I-9);
2-(5-(1,2-dithiolan-3-yl)pentanamido)-6-(2-hydroxybenzamido)hexanoic acid (I-11);
3-hydroxy-2-(hydroxymethyl)propyl 2-(5-(1,2-dithiolan-3-yl)pentanamido)-6-(2-hydroxybenzamido)hexanoate (I-12); and
N-(2-(2-(5-(1,2-dithiolan-3-yl)pentanamido)ethylamino)ethyl)-2-hydroxybenzamide (I-24).

4. A pharmaceutical composition comprising a molecular conjugate comprising a lipoic acid and an ortho salicylate wherein the lipoic acid and the ortho salicylate are conjugated through at least two amides and a pharmaceutically acceptable carrier.

5. A pharmaceutical composition comprising a compound of claim 2 and a pharmaceutically acceptable carrier.

6. The compound of claim 2, wherein $W_1$ and $W_2$ are each independently NR, wherein R is hydrogen.

7. The compound of claim 2, wherein m is 0.

8. The compound of claim 2, wherein m is 1.

9. The compound of claim 2, wherein L is —S—S—.

10. The compound of claim 2, wherein L is —O—.

11. The compound of claim 2, wherein L is

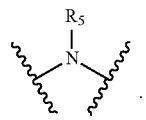

12. The compound of claim 2, wherein L is

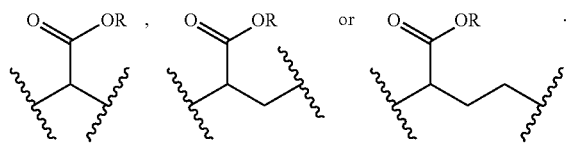

13. The compound of claim 2, wherein n, o, p and q are each 1.

14. The compound of claim 2, wherein two of n, o, p and q are each 1.

15. The compound of claim 2, wherein Z is

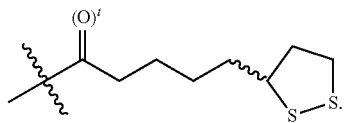

16. The compound of claim 2, wherein Z is

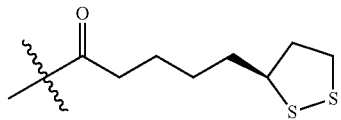 [SMILES: *C(=O)CCCC[C@H]1CCSS1]

17. The compound of claim 2, wherein Z is

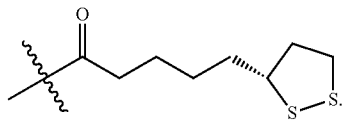 [SMILES: *C(=O)CCCC[C@@H]1CCSS1]

18. The compound of claim 2, wherein $W_1$ and $W_2$ are each NR, n, o, p and q are each 1, t is 1, L is —S—S—, and each R is hydrogen.

19. The compound of claim 2, wherein $W_1$ and $W_2$ are each NR, n, o, p and q are each 1, t is 1, L is —O—, and each R is hydrogen.

20. The compound of claim 2, wherein, $W_1$ and $W_2$ are each NR, n, o, p and q are each 1, t is 1, each R is hydrogen and L is

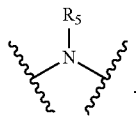

wherein R5 is $C_1$-$C_3$ alkyl.

* * * * *

UNITED STATES PATENT AND TRADEMARK OFFICE
CERTIFICATE OF CORRECTION

| | |
|---|---|
| PATENT NO. | : 8,946,451 B2 |
| APPLICATION NO. | : 12/898467 |
| DATED | : February 3, 2015 |
| INVENTOR(S) | : Jill C. Milne et al. |

It is certified that error appears in the above-identified patent and that said Letters Patent is hereby corrected as shown below:

In the Claims,

In claim 2 at column 62, line 53, delete "or" before the word "halogen".

In claim 20 at column 64, line 33, delete the "," following the word "wherein".

Signed and Sealed this
Ninth Day of June, 2015

Michelle K. Lee
*Director of the United States Patent and Trademark Office*